United States Patent
Tei et al.

(10) Patent No.: US 7,659,387 B1
(45) Date of Patent: Feb. 9, 2010

(54) TRANSGENIC MAMMALS INTRODUCED A PERIOD 1 PROMOTER THAT CONFERS RHYTHMICAL EXPRESSION

(75) Inventors: Hajime Tei, Tokyo (JP); Yoshiyuki Sakaki, Yokohama (JP); Shin Yamazaki, Nashville, TN (US); Michikazu Abe, Tokyo (JP); Ri-ichi Takahashi, Tochigi (JP)

(73) Assignees: University of Virginia, Madison Hall, Charlottesville; Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 10/130,659

(22) PCT Filed: Nov. 17, 2000

(86) PCT No.: PCT/JP00/08127

§ 371 (c)(1),
(2), (4) Date: Mar. 5, 2003

(87) PCT Pub. No.: WO01/36618

PCT Pub. Date: May 25, 2001

(51) Int. Cl.
 C07H 21/04 (2006.01)
 C12N 5/06 (2006.01)
 C12N 5/10 (2006.01)
 A01K 62/027 (2006.01)
(52) U.S. Cl. .............. 536/24.1; 800/3; 800/13; 800/14; 800/18; 435/325
(58) Field of Classification Search .............. 536/24.1; 800/14, 3; 435/6, 25
See application file for complete search history.

(56) References Cited

U.S. PATENT DOCUMENTS 5,663,483 A * 9/1997 Chiang .................... 800/9
5,958,676 A * 9/1999 Olivo .................... 435/5
6,555,328 B1 * 4/2003 Keesler et al. ............ 435/15

FOREIGN PATENT DOCUMENTS

WO  WO 99/57137  11/1999

OTHER PUBLICATIONS

Gekakis et al. Role of the CLOCK protein in the mammalian circadian mechanism. Science. Jun. 5, 1998;280(5369):1564-9.*
Yamaguchi et al. The 5' upstream region of mPer1 gene contains two promoters and is responsible for circadian oscillation. Curr Biol. Jul. 13, 2000;10(14):873-6.*
Arnone et al. The hardwiring of development: organization and function of genomic regulatory systems. Development. May 1997;124(10):1851-64.*
Holschneider et al. Genotype to phenotype: challenges and opportunities. Int J Dev Neurosci. Oct. 2000;18(6):615-8.*
Doetschman T. Interpretation of phenotype in genetically engineered mice. Lab Anim Sci. Apr. 1999;49(2):137-43.*
Sigmund CD. Viewpoint: are studies in genetically altered mice out of control? Arterioscler Thromb Vasc Biol. Jun. 2000;20(6):1425-9.*
Wall RJ. Trsngenic Livestock: Progressand prospects for the future. Theriogenology 1996; 45:57-68.*
Chilov et al. Hypoxia affects expression of circadian genes PER1 and CLOCK in mouse brain. FASEB J. Dec. 2001;15(14):2613-22.*
Brown, T. "Hybridization Analysis of DNA Blots" in Current Protocols in Molecular Biology John Wiley & Sons, Inc., 2003.*
Lindblad-Toh et al, Nature Genetics 24(4):381-386, 2000.*
EMBL Accession No. AB030817 (May 31, 2000).
EMBL Accession No. AB030818 (May 31, 2000).
EMBL Accession No. AF102137 (Aug. 24, 2000).
Geneseq Accession No. AAZ34628.
Hida, et al. (2000). Genomics 65: 224-233.
International Search Report for PCT/JP 00/08127, Aug. 6, 2001.
Kuhlman, et al. (2000). Neuroreport 11: 1479-1482.
Stanewsky, et al. (1997). EMBO J 16: 5006-5018.
Taruscio, et al. (2000). Gene 253: 161-170.
Tel, et al. Nature 389: 512-516.
Yamazaki, et al. (2000). Science 288: 682-685.
Kuhlman et al., *Society for Neuroscience Abstracts*, Abstract #824.6, 29th Annual Meeting of the Society for Neuroscience, USA, Oct. 23-28, 1999, 25(1-2):2065 (1999).
Sangoram et al., "Mammalian circadian autoregulatory loop: a timeless ortholog and mPer1 interact and negatively regulate CLOCK-BMAL1-induced transcription", *Neuron*, 21:1101-1113 (1998).
Sun et al., "RIGUI, a putative mammalian ortholog of the drosophila period gene", *Cell*, 90:1003-1011 (1997).

* cited by examiner

*Primary Examiner*—Joseph Woitach
*Assistant Examiner*—Kevin K. Hill
(74) *Attorney, Agent, or Firm*—Ingrid A. Beattie, Esq.; Cynthia Kozakiewicz, Esq.; Mintz, Levin, Cohn, Ferris, Glovsky and Popeo P.C.

(57) ABSTRACT

The present invention relates to an isolated Period 1 (Per1) promoter DNA inducing rhythmical expression of a gene operably linked thereto. This invention also provides a DNA comprising a Period 1 promoter DNA and a gene operably linked thereto, the gene being under the regulation of the promoter DNA. The present invention further provides transformants and transgenic mammals into which the DNA has been introduced. The transformants and transgenic mammals are useful in the screening of pharmaceutical drugs against diseases and disorders pertaining to the circadian rhythm.

19 Claims, 6 Drawing Sheets

SEQUENCE LISTING

<160> NUMBER OF SEQ ID NOS: 2

<210> SEQ ID NO 1
<211> LENGTH: 8712
<212> TYPE: DNA
<213> ORGANISM: Artificial Sequence

```
<220> FEATURE:
<223> OTHER INFORMATION: Description of Artificial Sequence:
      artificially constructed sequence
<220> FEATURE:
<221> NAME/KEY: Sequence derived from mouse Per1 promoter
<222> LOCATION: (23)..(6787)

<400> SEQUENCE: 1
acgcgtgcta gcccgggctc gagatccgat gccctcttct ggtgtgtctg aagacagcta      60
caatgtactc atacaaatct taaaaacaaa caaacaaaaa ttagattttc aaagttgggc     120
agagccaggt ggattggcaa tctccaggtt tgggggcagc caggtctaca gagtgagttc     180
tagaacagcc agagcaacac agagaaaccc tgtctgggcc gggcagtggg ggcacacgcc     240
tttaatccca gcagaggcag gtggatttct gagttcgagg ccagcctagt ctacagagtg     300
agttccagga cagccagggc tacacagaga agccctgtct cgaagaaaaa agaaaaaaag     360
aagaaagaaa cctgtctgga atacacccc cgccccgcaa aagggtgtca ttggaaatta     420
tttcagaggt tctaaagtac tgaggtgtct tacagcctat cctaaattct acctttatgg     480
agagtttaaa taaggctttt tgcatttaat tcttggaatt acttctaggt ttaatgtctc     540
cataggcctt acaataccaa gctacccttta tggtgtcaga gacctgggtt cagactttag     600
ctcttttatc aatatacata atctaattcc gacagattac gtaacctctc agcctctttt     660
gtgaggttat gggtagtgag ccggccttct tgggagtctg caagaagggg ctggccagcc     720
aggcccaaag aaaataaata ggaggcgact gtcatttcac cgtcattgtc atgcaatcta     780
atgatatctt cagtgtagtg ctcagatttt taagctttgg ggatcactag agacacaaag     840
ctcaggcacc agaaacctct tgtaatgcca gagtctccaa agtatgccca ctacgccata     900
gcctgtcaga tctacgcctg cgtacaagtc gctcggcacg cctgcgcaga ctccgcagta     960
ttgggtaagt gtcgtcaagg aaaatcccca gcttctgggt aaacaagttg ccgcgtgagc    1020
cagcctgcac gtgttcccta cagctctgag ccctctcagc ctatgagaaa gtttttaggg    1080
cagggctggc atttgcgtca ctgatttagg cagggcgggg ttgtctctgc agccagtaaa    1140
aatgttgaga gtgggtgggg gtgtggcttc cggtcagatg tccaatcaac gagttggggc    1200 gccccgccc tcacgtggct ctatcactac cggttgtcat attgtccaat gggaaaatga    1260
ctgagttctg aaatgccaat ggttgcttta caagggcttg ccggctgcac gcggagcggg    1320
gcatgggttg gcgtctctga gccaataagc tagggaggcg tgacagaacg ggcggtggga    1380
gggcctcgag gactctgtgg aggagcccca ggagtgaaga aatttggagt ctacgtgcgc    1440
tcggaactgt gagtagcccc ttactctgga gccgtcgaac ttgtgttttt ggggaggtgc    1500
gctcgaccaa aagggtgtc agtggcgtgg tgtgtgtgag ggatcatgca aatgtgaatt    1560
agctgcagaa caaatgccta atggttgtgg agaaagagac cacaagttca actctagggg    1620
aacatgaatg agagttacca gcaacagatc tctcaccact ctagggtccc tggacactaa    1680
tgcctagcgc agggtgctca gaagccccta gccatccgag ggagccgaag cgcctgcgat    1740 atgaccctg agagctggtt atggtttggg gtaggctccc taaacacttg gaagagaccg    1800
ccccggtagg gcgggcggga acgtagtttg gtgatctgag aaaggctggt gtgttgattt    1860
gaccgaaagg ctgtctcatc acgactatag gtggtatcgt ggcctcaggg acatgctcga    1920
aaataggaat gggctagtaa tttgttggat tctgaaaggg aggataaggt ggagggtttc    1980
tgtacaccgt ttcgtctact cttcttaagc tgctagaggt ggagttacca aaggactgct    2040
ctggtgtcta gacgttcggt cgggcagagg tgagggagga gagggaggaa gtgagattct    2100
```

```
taggaaagca gtgtgcctgc aggcttctcg agtgatctcg ggttttgagc atagaaacga   2160
accatgatgg tgcgcacgga gcacaaacaa tgccttgaga tcaggctaag gggagagaag   2220
gagacggaat tggatatagc ctgtattcta ggcaccaagc ttagaaacag gggaatactc   2280
cccccgcagt cctacggtgc tggaatgcag tgtagaggtt tggtaacact ttacagggtc   2340
cctaagccag caggacaagc catcattagg gcttgaacct tgggctccat tattaggaag   2400
ctgagaatga agcagacaat taaggcaagt ttagtaacta cctactaagt cttagttttt   2460
ccttatgaca tcagggtgat acttaccttc agttgtttgg gggcttacat gagaacaata   2520
tgtgtaaagt tcttagcaca gcgcttggat catttacaaa cacaaactat aaggtaacaa   2580
aagaatagcg atagagttgg ggatttatgt gcatgctgtg ccagagagc aatctccatc    2640 ttctgttttt ctgcaagttt tgatgactcc tcttttccct ctccctgatt ttttttttt    2700 tttttttttt tttggtcttc gggcaccagc ccaaattcca tcattcctcc ctgtattcct   2760
ctcccaagat ctgggcccca gactgaggca atttgctgtg tcccagtttg acttcatctt   2820
aaatccattc tctctgacca ccccccccc ccacctattc tgtgctgtaa tagtaactag    2880
aaagtctgcc tctaaagagg ggccccaggg aaggagcaaa ggtgcgttct ctctcagaac   2940
ctaggcctcc aatttacccg ccctagctct ttggtacctg gccagcaacc gtgtacagtc   3000
tggtgacggg gaaaagccaa tgccaggagt tttaagaccc agctgaggga gggtaaaagt   3060
aggtcccgca aagagaacca ggcatggggg cggggagggg ggaccccctt cctcctaact   3120
gtctctccag gaattttggg cttttgtaca ggaccgctgt cgttgggttg ggggaggcgc   3180
caaggctgtg tgcatgtcct gggccatcag ccaagagaac acgatgttcc ctagtgcgct   3240
ggccgccgcc ctctggggct ggccgccctcc caaaccgctg cctctccagc ctccctgccc   3300
cacattcccc agctgcctcg ccccgcctcc tgcctccgct ttgacgtcac ctccctctcc   3360
tgcccccgct tctccattga cggcagcaga gcctggttac tgtgggggac tgatgaggcc   3420
cgacagcctg ggccttggga tcaggttggg gctgtttgga gtgctgaaac cttttgtctg   3480
tgtaaatgac agatagggaa gtgggcgagc aatggctgct tgggtcagag gaatcacacc   3540
taaatccttg agagctgtgg aaagagaaag gggtctggaa aaaaaaaaa ggacagcaca   3600 cggtcacaac gcagtacgag ggggcaggag agcagcatca ttttcaggag gaggaagctg   3660
agcactcagc ctcccgtgtc ttttgttttc tgtgtttccc tgcttctgtt tttctgggtt   3720
attttataac aggtctgtgt cccagcattt ctatagaacc ttgtctcgcc cgcctcctct   3780
aagggaaaca ccattgttaa ggaaagcttt agccacgtga cagtgagggg cgtgcactta   3840
acagctgatt atgtcagccg ctgcgtgttg gcctcttcac ttgccaccta cgtttgcagg   3900
gaagcctgag aactactcag cccaggccta gggaagggga ctctgtcact gtagctctcc   3960
tggacccaga ctggcatgtt gtccccccct ccccaaaatc gagtctctat tctctttta   4020 tgaatcaatg ctctactttt cttttgaaaa cataatttgt tgcctcctct cctgaggctc   4080
tctctcccct acctatcctt aatagaaaca gagccatcct gtttaccgag catctactgt   4140
cagtcctgac gctgagacgt acttaccttca ctgctgagaa tacagtaaat gagacagatg   4200
ggcttgctgc tgggttcatg aaccttggct tttgtattct aagcagcagg aataaaaagc   4260
ccaataaaaa gcccttgcca cccagccacc catcctttt ctgcctactg ctgcaactgc    4320
cctctctgct gccccttttg tagtactggc ttcctggtcc ccactttgg ggcagccta     4380 aatgtgggtg gctgcatcct ctgcagaggc agcactagtc accaagtagg cttcctggag   4440
accttttctc tgattggcta gtgaagcacc tgcttttgtt tcctttcaca gtagccattg   4500
```

-continued

```
gctttccctg tcctttccgt ttgtccgtat ccttccatca cccactcacc ccttaacgac    4560
acgtgggccc tcaattgccc ttctctcagg atctgaaggg tcagaggaaa gggttggatt    4620
ctttataaca aggctgggga gaggccaggg aatgtcagtc taggtttttc tctctcccac    4680
ttcccttggg tagcagacat ttcattcacc cggcaccagg acaggtgtct tgttctgcca    4740
agctggtcag tttaggaagt aggttttctct tgagcacttc ctgtggccca ggtatcctcc    4800
ctgaaaaggg gtagtttccc tccctcactt cccttttcatt attgacggtg tgagacatcc    4860
tgatcgcatt ggctgactga gcggtgtctg aggcccttca gcccagcacc agcacccaag    4920
tccacgtgca gggatgtgtg tgacacagcc ctgacctcag tgggggccag tagccaatca    4980
gatgccagga agagatcctt agccaaccgg gggcggggcc tgcggctctt cgggcagaag    5040
gccaatgagg ggcagggcct ggcattatgc aacccgcctc ccagcctcgc ggagcttctg    5100
ggttgcgggc cgaaacggca gcggatgga gggcgctcga acggccaggt agggatccct    5160
gctgctgcaa tcctagggtt agtctttgtc ccggagcttg gccgccacta cttccaacgt    5220
gatgggtcgc tttcagctct cagagagcaa acaataatc tgccttttcct gtcactatcc    5280 accctccccc gcccctgggc cctaggtgtt caactcaacc cgtcacgggt tgtctgcgtt    5340
tgttattcgt tcacctaatc tcctcctctg ctcctccaga gcagccatcc tgaacctaag    5400
agacctttag cgaacacgac ccctttacac attgctcgac actcgggagt ccatgggttt    5460
gccctagccc aaagacccc ttcaggcttc tgcgctccct gtcttcctcc ctccaattcc    5520
tggcctcgtg ccggtcgtga tgtcaaccgc ttcaggctgg aacatcctgt tctcagcgct    5580
agttcttgct gttggccaca gccttccttc cctttctcc tggcgctcag aaaatacttg    5640
ggatgggggt gtggttagac agggagtaga ggaaaaacta tatatgctgg ttgttgtgtg    5700
tcccctatct atgtggtagt agggttaact agaaaagtaa gggacgaagg aagatgcctg    5760
agtcgttgcc tatggcaagt ggtaactcca gtcctggtgt ttgggagtgg gcaggggctt    5820
gagaaagaaa agcagtgtct tgatcagaat aatgttcgag gcaagagcga ggatgggggc    5880
gtttccacaa agagcagagg ccgagtgggg aagctaggac ttgctcctgg agttcctcta    5940
gtttgttact cttcacatgg ctcctaggct cttttgggccc tgggaatttg ttatggtggg    6000
tgttcttctc ctccccgctg ccctgaacct tgttagccag tatgagggtg tgttggccag    6060
tataggactg ggtctgtttc ccacttccac gaagatgggg attgggggag gagtcgttcc    6120
tgccctcctg tggtccctcc agcaaccgct gagctcagcg gctgacgtcg gtttccctgg    6180
cgaccgcggc tgtggcggaa gcgcgtggtg gggccaggca catcggcgcg catgtgcagc    6240
gggggtggca ccgccccggg ataaaattag cccggaagcc taaatatagg aggcgatcag    6300
ctcaccccct gctccgaggc tcagagtcc cagaccaggt ggggacctga tgagaatttg    6360
ggcataggaa acctgcaagc tttgacccctc agctactgtt ctagtcgatt gttcaggctg    6420
tactcattcc acactggcaa ggggtgtaag agatggccta cgagagctgc ctttctacct    6480
gtggtatcct taggtccccc taaggaaata gaacatattt ctattgcaag ccccaggcct    6540
gagtcacaac agtgaggggc aggcagagga aggactgggt gtagccagca gatgctgtgg    6600
ggttaatagc tcagctttg ctaaacattc cttttttggtt tcttttttcta ggtgtcgtga    6660 ttaaattagt cagccctcag agacaggcgt cctacctcct ttatccagac ctcaaaagcc    6720
ccgttgtgca cccgtggtgg cttcttcacc ttccctgttt cgtcctccac tgtatggccc    6780
agacatggaa gacgccaaaa acataaagaa aggcccggcg ccattctatc cgctggaaga    6840
```

-continued

```
tggaaccgct ggagagcaac tgcataaggc tatgaagaga tacgccctgg ttcctggaac      6900
aattgctttt acagatgcac atatcgaggt ggacatcact tacgctgagt acttcgaaat      6960
gtccgttcgg ttggcagaag ctatgaaacg atatgggctg aatacaaatc acagaatcgt      7020
cgtatgcagt gaaaactctc ttcaattctt tatgccggtg ttgggcgcgt tatttatcgg      7080
agttgcagtt gcgcccgcga acgacattta taatgaacgt gaattgctca acagtatggg      7140
catttcgcag cctaccgtgg tgttcgtttc caaaagggg ttgcaaaaaa ttttgaacgt       7200
gcaaaaaaag ctcccaatca tccaaaaaat tattatcatg gattctaaaa cggattacca      7260
gggatttcag tcgatgtaca cgttcgtcac atctcatcta cctcccggtt ttaatgaata      7320
cgattttgtg ccagagtcct tcgataggga caagacaatt gcactgatca tgaactcctc      7380
tggatctact ggtctgccta aaggtgtcgc tctgcctcat agaactgcct gcgtgagatt      7440
ctcgcatgcc agagatccta ttttggcaa tcaaatcatt ccggatactg cgattttaag      7500
tgttgttcca ttcatcacg gttttggaat gtttactaca ctcggatatt tgatatgtgg      7560
atttcgagtc gtcttaatgt atagatttga agaagagctg tttctgagga gccttcagga      7620
ttacaagatt caaagtgcgc tgctggtgcc aaccctattc tccttcttcg ccaaaagcac      7680
tctgattgac aaatacgatt tatctaattt acacgaaatt gcttctggtg gcgctcccct      7740
ctctaaggaa gtcggggaag cggttgccaa gaggttccat ctgccaggta tcaggcaagg      7800
atatgggctc actgagacta catcagctat tctgattaca cccgaggggg atgataaacc      7860
gggcgcggtc ggtaaagttg ttccattttt tgaagcgaag gttgtggatc tggataccgg      7920
gaaaacgctg ggcgttaatc aaagaggcga actgtgtgtg agaggtccta tgattatgtc      7980
cggttatgta aacaatccgg aagcgaccaa cgccttgatt gacaaggatg gatggctaca      8040
ttctggagac atagcttact gggacgaaga cgaacacttc ttcatcgttg accgcctgaa      8100
gtctctgatt aagtacaaag gctatcaggt ggctcccgct gaattggaat ccatcttgct      8160
ccaacacccc aacatcttcg acgcaggtgt cgcaggtctt cccgacgatg acgccggtga      8220
acttcccgcc gccgttgttg ttttggagca cggaaagacg atgacggaaa agagatcgt      8280
ggattacgtc gccagtcaag taacaaccgc gaaaaagttg cgcggaggag ttgtgtttgt      8340
ggacgaagta ccgaaaggtc ttaccggaaa actcgacgca agaaaaatca gagagatcct      8400
cataaaggcc aagaagggcg aaagatcgc cgtgtaattc tagagtcggg gcggccggcc      8460
gcttcgagca gacatgataa gatacattga tgagtttgga caaaccacaa ctagaatgca      8520
gtgaaaaaaa tgctttattt gtgaaatttg tgatgctatt gctttatttg taaccattat      8580
aagctgcaat aaacaagtta acaacaacaa ttgcattcat tttatgtttc aggttcaggg      8640
ggaggtgtgg gaggtttttt aaagcaagta aaacctctac aaatgtggta aaatcgataa      8700
ggatccgtcg ac                                                         8712

<210> SEQ ID NO 2
<211> LENGTH: 6573
<212> TYPE: DNA
<213> ORGANISM: Homo sapiens

<400> SEQUENCE: 2
ccaggcagtg ctcaggattt cgcactgcca actcaaattc cttccaggtt taagagttcc       60
catgggcccc aggacccgcc tgctttatgg tgtcgggac ttgggttcaa gttttcgcct       120
tgttactgac tagcgtgtta caggcgaaca gattacgtaa ccccctgca tctcggtctc       180
atttgtgagg cggggggagt atgtgagctg gcctcctcag agtttgtgag aagcgcctgg      240
```

```
cctggcccgc agaaaacaat caggaagagg ctctcttatt ttcatcgtca ccaagacacc    300
gtgctgagat ctgaagaccg cttcaccta  atactctcac cttccagctt cagggagcct    360
cggtgggacc cagggccgga accccagcgc cagaggcgcc tagtcacgcc cgggtctctg    420
tacaaagtgc gccttatacg ctgccaccgc tcacggctgc gcctgcgcag atttagcagc    480
cgtggttaag agtgtcgtca aggaaaatcc ccagcttctg ggtaaacaag ttgccgcgtg    540
agaccgccgg cacgtgtacc ctacagctcc aagacctctc agcctatgag aaagcttgga    600
gagcgggact ggcatttacg tcaccaatct tggcaggtcg ggggttattt ccccagccaa    660
taagaacctc agaagtgtcg agggcgtggc ttccggtcag gcttccaatc cccgcgttgg    720
ggcggcccct ctctcacgtg tatctctccc gcccccgttg gcctgctgac caatgagaag    780
acgatggcgg ccggagtgcc aatggaggct gtgcgggggc cggcggctgc acgcggcacg    840
gggcatgggt cggcgcccct aagccaataa gcgtgggggg cgtggcagcc cggcccgtgg    900
gcgggtttgg aggagccagt gtaatgctag aagtcctaga agaaatttgg agtgtgcgtg    960
cgcgccgagc ggtgagtgct cggggatggg ggagagatgc ggggcgatcg gtgtggactt   1020
ttccggggtg gtgtggtcgg ttaggaaggt gttagagtgt gtgtgtgtgg gatcatgcaa   1080
atacgtgata actgcggtgg gagctctgat ggttgtggag aatagggacc gtgaactcag   1140
gtctagaggg acggggtggg agttagtgac atcagatccc tcgcccccgt ggagtccctg   1200
gacacttgac tgcccggggg gaagggctcg gaagcctctg cgacctgagg gagctccctc   1260
tcaggtcgga actgaaggag cccctgctcc cagggtgttt gggtggtctc cttaaacact   1320
tgaaagaggc agaggttcgg aggccggagg gaggccctgg tagggcaagt cggagggtac   1380
caaaggggttg gcatgctgat atgagaaagg atggtgtttt aatttgtgag acccagagct   1440
agtcacatta cggctccggg cgtctttctc atgttaagcg gaagggttta ggcctcagag   1500
tcgtccttga gaatagacgt ggggtagcaa ctattgagtc ctgagaggat agggttgggg   1560
tttgggcaga ttggctgtgc acgtcttcct gagcccctag aggtggggag gcaccaacag   1620
ggtgtttttg tatctgtctg tacaaacaac caggccaggc gtctggtaaa gttggcctga   1680
ggtaaagtag aaaagtgagg aagtgggctt cgtaggaaat cattggggct ggtggctgct   1740
tgggtgatct caagcacttt gtgagcctgg gaaaacgggc tatgatgtta agtgtgtggg   1800
gagtgcaaac agtggcttcg gatcaggcct aaggcagaga aaggggttgg atggagtctg   1860
tgttcctggc accaaactta gaattggctg gatatttgag aggccaggtt tgccagtgct   1920
ggaatgcagc ttacaggttg gttaacacct cacaggttcc tcaagggtaa gaaaccagaa   1980
tgacaagcca ttattagagt tcagattttt gaatcctggg ctccatttgt taagagcttg   2040
agaccatgtt atgaggcact ggacaagttt agtaacttcc gtgccttagt tatccccccat  2100
ggaatgggga taataatacc tatctcacgg ggttgttctg gggatgaaat aagataaatat  2160
aaagtgctta gcataatgcc tgggttatgg tgagagattt atgtgaatgc tgtggctggg   2220
aactagtctc atattctcaa gttttttctgc aagttttgat ggcgtcccat ttctctcttc   2280
ctggctcttt tggtcttcag gcagcagtcc aaattccctc attcctccct tctagccctc   2340
tcccaggatc caggccctag actgggccac ttgctctgtc ccagtttgat ttttcatcc    2400
taggcccctt ctcctccctg tccgcgcccc tctcccttttc ccccgcccg ctgtcataat   2460
aagagattca ggctctgaag gggcttctgg aaggtagcaa aggtgcgtcg tgttctctcc   2520
cagagacagg acctccaact tctccgccct gggtctttgg taccaggcca gcagatgtgt   2580
```

```
acagtttggg agagaggaaa agccagagct gcaggaacaa gctgaggagc gggcagatgg   2640
gagtcctgaa aagagagcca ggcgtggtgg ggggaggtgt ggggaggggg ccccttcct    2700
actaatcctc tctccaggaa tccctggctt tgggacagga cggctgtcgt tttgttgggg   2760
gaggcgccca ggctgggtgc atgtcctggg ccaccagcca agagaacatg atgttcccaa   2820
gtgcgctggc cgccgccctc tcgggctggc cgcctcccaa accgctgcct ctccagtctc   2880
tccagcctcc ctgcccaca ttccgaggca gcttcgcccc gcccccttct tccgctttga    2940
cgtcactgct gtctcccgcc ccctcgcctc cattgacggc agcagggcct ggttactgtg   3000
gggacggtga agcaggacaa caagagtcct tgggagcaag cggggggctgc tggagggctg   3060
gagccttttg tctatgcaaa agacagggag atggaggcgg gagatcaagg actgcctggg   3120
ttaggggaga tcacacctaa atccctgaag ggggagaaaa accatgtttc cagggaagag   3180
gtatctgcaa acgagataag gccaaagcca cagtatgagt tggggtggag aggatcattt   3240
tcagggagag gagactgaga atccaagctc ctgaatcttt tttttttttt ttaatagaga   3300
cggggtttct ccatgttggt caggctggtc tcgaactcgc tacctcaggt gatccgcctg   3360
cctgggcctc ccaaagtgct gggattacag gccaccgcgc ccggcctcca ggctcctgaa   3420
tcttttgttt tcctgtttcg attttttctgg gttaatttat aacacgatct tgtctcagct   3480
tttccacaga gccctcccct tcacccttcc ctcattgttc aggaaagctt aggcacgtg    3540
acagtgaggg gagtgccccc acaatgatta tgtcagcagc tgcttggagg cctgttcatc   3600
tactacccac gtttccaggg agccctgcga ggaactactc atcacggtcc tggatggagg   3660
gggctgtgta actgcagctc tcctgagccc agactaacat tttattgcct gcaaatcgtg   3720
cccctgttct ctttctagga ctactcatct cttttagaga atcagaattc ccagcccct    3780
ttctcctgtt gacactcttt tcccacctcc ccaacctatc cttgtttaaa aaaaaaaaa    3840
tcatgtttat cgatcacttg ccatgtgtca ggtcctgtcc tgggctctgg agactacagt   3900
gaatgagaca gatgacgttc cgtctgggcc cctggagttt ggctttctct tttccaagca   3960
gtggaaatat gaagcccttg ccaccccaca tttctctgtc tagggcccca gctggcctct   4020
tctctgggcc atccccttgg tccctctgta gtcctggctt cctggccccc acttttgggg   4080
cagctttaac tgtgggtggc tgcgtcctct ggaggaaagt actagacacc acgtaggctg   4140
cccggagacc ttgtctctga gtggccatag aagcacctgc cattgtttcc cttcacagcc   4200
actattggct ctggttgccc cttccattgt ccgcatcctt cctccaccca ctcacccacc   4260
ggtcacacgt ggacccttaa ctgtcctctc ccaggatttg aagtgtcaga ggaagtgctt   4320
cggttaaagg gcttcattat gtagaacgaa ggttgggagg gaacaaggtt gggaaaggaa   4380
cccaggagag gcccaggcag gtttctgtct ctcccctcct ctcaaggacc acccatctca   4440
tccagcgtgg cctaacttgc agcgccattc cttttcctca cccttggaaa ggcgaagatg   4500
ccaagatgtt gtgttctgca aggctagtgc gttcaggaag tagacaagtc ttgagcacct   4560
accccgggcc gggcttttc cctaaagagg cgcagcgtat ctccctctct cctcccttcc    4620
attattcaat gtgcaagcgt cctgcgccca ttggctgggc ggtgtctggg gctcttcagc   4680
ccagcaccag cacccaggtc cacgtgcgcc cgtgtgtgtg acacagccct gaccttagtg   4740
gagaccacta gccaatcagg cgccgggaag agatccccag ccaatcgggg gcgggcctgc   4800
ggctccgtcg gcaagaggcc aatgaggggg cagtgcccgg cattatgcaa cccgcctccc   4860
cgcccgcccg gtgagcttc cactcggctg cgggctggag cggcggcggg caggcgtgcg    4920
gaggacactc ctgcgaccag gtaggcatct ctgcggccat cctggggccg atctccgtcc   4980
```

```
                                                  -continued ctgagccgga  ccgctgccac  ttccaatctg  atgggctact  ttcggcccag  gcagagggca  5040
cactgtcgtc  cttaccgcta  cccaccctct  ccctgccccc  aaggaccgaa  gtcctcctcg  5100
aaatcttgca  ccgggagtct  gcactcctga  cccactcatc  ttacctccag  cttgtcccca  5160 cctcccgtc   ccagctttcc  cggccccaca  gccgactctc  agcgggcatg  ccccggtctt  5220
cttgctcgtt  actcgagggg  ccccaggttt  gccccggtac  caggaccccta ttaggctttc  5280 agcgctcccc  gtgtctctgt  tctccagtcc  ctggccctgc  gccgcctgtg  atgtcagccc  5340
acttcggact  agaacatccc  gttcccagcg  ctggttcctg  ctgttggcca  caaccttccc  5400
ttttcccctg  gcgctcagaa  aatgctcagt  agtaggggtg  tggttggacg  gggagtaggg  5460
gaagaaagat  ctgttggctg  ttgtgtgtct  tctgcccaag  gcttgggtt   ggtgggggg   5520 tctggccaga  aaagtagggg  actgaagaga  gaggatcctc  gggtccttga  cgatggcagg  5580
ttgccggctt  cggtccttgt  ggtggggaag  cagcgcaggg  gctaaagaag  gaaaggttgt  5640
gttgtcttga  ccagaatgac  tgggatccag  gcgagagtca  ggttgagggg  cttttgcgcc  5700
gagggcagtg  gccgttgtgc  ttcgtcctgg  ggaagccagg  accaaccctg  ggatcctaat  5760
aggccgtccc  acttcttacg  gccaccgagc  catcctggga  ctggggatat  gtaagggatg  5820 cgtgacccc   ccggccgcgc  ccaccagtgt  gagagtgggc  cgttccccca  cttccgccgg  5880
gaaatggggg  aggggtcgct  cctcccgccc  tcctgtggtc  cctccagcaa  ccgctgagct  5940
cagcagctga  cgtcggtttc  cctggcgacc  gtggcggcgg  cggaagcgcg  tggtggggcc  6000
gcgcacgtcg  gcgcgcatgt  gcagcggggg  tggcaccgcc  cccggataaa  attagcctgg  6060
aggcctaaat  ataggaggcg  accagctcac  ctcctgctcc  gaggccttgg  aggcccacgc  6120
agagtggaca  cctaatggga  acttgggaat  gggaagtgtc  caggttttttg tctacagccg  6180 tggttctcat  tgactgctca  ggccatggtg  gcagggatg   tgaaggaagg  ccccggagaa  6240
ccttctcccg  ctggcagtcc  ccctaagggt  acaggagaca  tcctgactcc  ccattggaag  6300
ccccaggcct  gggttccact  cccatcagtc  ctgcaggagg  ccaggcaggg  ggaaggtctg  6360
agtgaagcca  gcaggtgctc  tggaattaaa  ccagctttct  gcaagccctg  cttcctggtc  6420
tccctctcca  ggtactggct  gtgatcgaac  ttctcaaccc  tcagagactt  agatcttcca  6480
cctcactccc  tcagccaagc  ctccaggccc  cctcgtgcat  ccgtggtggc  ctctctgcct  6540
tctctgttct  gttctccca   tggcccagac  atg                    6573
```

TRANSGENIC MAMMALS INTRODUCED A PERIOD 1 PROMOTER THAT CONFERS RHYTHMICAL EXPRESSION

This invention was made with United States Government support under Grant No. MH 56647, awarded by National Institute of Health. The United States Government has certain rights in the invention.

TECHNICAL FIELD

The present invention relates to an isolated Period 1 (Per1) promoter DNA inducing rhythmical expression of a gene operably linked thereto. It also relates to a DNA construct comprising a gene operably linked to the Period 1 promoter, in which the gene is under the control of the promoter DNA. The present invention further relates to transgenic mammals into which the construct has been introduced. The transgenic mammals are useful in the screening of pharmaceutical drugs against diseases and disorders pertaining to the circadian rhythm.

BACKGROUND ART

The recent explosion of information concerning the molecular mechanisms underlying circadian rhythmicity in organisms as diverse as bacteria and mammals has left unanswered critical questions about the organization of circadian systems in multi-cellular organisms. At the same time, it has provided important new tools that can be used to answer these questions "A. J. Millar, S. R. Short, N. H. Chua, S. A. Kay, *Plant Cell*, 1992, 4, 1075; T. Kondo et al., *Proc. Natl. Acad. Sci. U.S.A.*, 1993, 90, 5672; J. D. Plauts, M. Kaneko, J. C. Hall, S. Kay, *Science*, 1997, 278, 1632".

Although the suprachiasmatic nucleus (SCN) is the dominant circadian pacemaker in mammals, a surprising number of peripheral tissues appear to contain the molecular machinery necessary for circadian oscillation "U. Albrecht, Z. S. Sun, G. Eichele, C. C. Lee, *Cell*, 1997, 91, 1055; D. P. King, et al., *Cell*, 1997, 89, 641; L. P. Shearman, M. J. Zylka, D. R. Weaver, L. F. Kolakowski Jr., S. M. Reppert, *Neuron*, 1997, 19, 1261; H. Tei, et al., *Nature*, 1997, 389, 512; N. Koike, et. al., *FEBS letters*, 1998, 441, 427; Y. Miyamoto and A. Sancar, *Proc. Natl. Acad. Sci. USA.*, 1998, 95, 6097; M. J. Zylka, L. P. Shearman, D. R. Weaver, S. M. Reppert, *Neuron*, 1998, 20, 1103" and, in a few cases, these vertebrate tissues have been shown to express circadian oscillations in the absence of the SCN "R. V. Andrews, *Gegenbauers Morph. Jahrb. Leipzing*, 1971, 117, 89; G. Tosini and M. Menaker, *Science*, 1996, 272, 419; A. Balsalobre, F. Damiola, U. Schibler, *Cell*, 1998, 93, 929; D. Whitmore, N. S. Foulkes, U. Strahle, P. Sassone-Corsi, *Nat Neurosci*, 1998, 1, 701". However, detailed relationships among the oscillations in multi-tissue systems remain unknown.

DISCLOSURE OF THE INVENTION

An objective of the present invention is to provide an isolated Period 1 promoter DNA inducing rhythmical expression of a gene operably linked thereto. It also provides a DNA construct comprising a gene operably linked to the Period 1 promoter, in which the gene is under the control of the promoter DNA, and uses of the DNA construct. Further objectives are to provide transgenic mammals into which the construct has been introduced, and uses thereof.

The present inventors hypothesized that the mammalian circadian system is hierarchically organized, with the self-sustained circadian oscillators in the SCN entraining damped circadian oscillators in the periphery, thus generating complex phase relationships among multiple overt rhythms that are suggested to exist "F. Halberg, *Cold Spring Harbor Symposia in Quantitative Biology*, 1960, 25, 289; M. C. Moore-Ede and F. M. Sulzman, in *Handbook of Behavioral Neurobiology* 4. *Biological Rhythms*, J. Aschoff, Ed. (Plenum Press, New York, 1981), pp. 215-241, chap. 12.", and are almost certainly critical to normal function. Predictions from this hypothesis include but are not limited to: 1) differential rates of phase shifting of the SCN (rapid) and such circadian output measures as locomotor behavior (slower); and, 2) the existence of damped circadian oscillators in peripheral tissues.

To test these predictions, the present inventors constructed transgenic rat and mouse lines in which luciferase is rhythmically expressed under the control of the mouse Per1 promoter, and have used them to study mammalian circadian organization. Light emission from cultured suprachiasmatic nuclei (SCN) of these rats and mice was invariably and robustly rhythmic. Circadian rhythm light emission from the SCN followed light cycle shifts more rapidly than did the rhythm of locomotor behavior. Liver, lung, and skeletal muscle of the rats also expressed circadian rhythms, which damped after two to seven cycles in vitro. These observations suggest that self-sustained circadian oscillators in the SCN entrain damped circadian oscillators in the periphery to maintain adaptive phase control.

The data presented in the invention indicate that in response to a light cycle shift, the central circadian oscillators in the SCN shift more rapidly than does at least one rhythmic behavior that they are known to regulate. This clearly disrupts the synchrony that is characteristic of the circadian system in the entrained steady state, and may be responsible for the impairments associated with "jet lag" and shift work. Taken together with the demonstration of the existence of damped circadian oscillators in several peripheral tissues, the phase shift results support our hypothesis.

Rapid shifts of central circadian pacemakers are predicted from theoretical considerations and has been demonstrated indirectly for *Drosophila* and rodents (C. S. Pittendrigh, in *Biological Clocks in Seasonal Reproductive Cycles*, B. K. Follett and D. E. Follett, Eds., John Wright and Sons Ltd, Bristol, 1981, pp. 1 to 35; M. U. Gillete, in *Suprachiasmatic Nucleus*. The Mind's Clock, D. C. Klein, R. Y. Moore, S. M. Reppert, Eds., Oxford University Press, New York, 1991, chap. 6; M. Takamure, N. Murakami, K. Takahashi, H. Kuroda, T. Etoh. *Phsiol. Behav.*, 1991, 50, 443; J. D. Best, E. S. Maywood, K. L. Smith, M. H. Hastings, *J. Neurosci.*, 1999, 19, 828). The data presented in the invention demonstrate directly that the expression of Per1, a primary molecular component of the circadian autoregulatory feedback loop in the SCN, rapidly follows large phase shifts of the entraining light cycle in either direction. Transgenic mammals of the invention enable the observation of the phase shifting trajectories of the peripheral oscillations following large phase-shifts of light cycles. The relationships between the trajectories in the peripheral tissues and the central pacemaker, or locomotor activities, can be also determined using the transgenic mammals of the invention. Furthermore, novel stimuli, genes, factors, and reagents that regulate circadian oscillators in multi tissues can be screened using these transgenic mammals capable of detecting circadian oscillation in the SCN as well as in peripheral tissues.

An objective of the present invention is to provide an isolated Period 1 promoter DNA inducing rhythmical expression of a gene operably linked thereto. It also provides a DNA construct comprising a gene operably linked to the Period 1 promoter, in which the gene is under the control of the promoter DNA, and uses of the DNA construct. The present invention also provides a host cell carrying the construct and uses thereof. Further provided by the present invention are transgenic mammals into which the construct has been introduced. The transgenic mammals are useful in the screening of pharmaceutical drugs against diseases and disorders pertaining to the circadian rhythm.

Specifically, the present invention relates to:

(1) an isolated Period 1 promoter DNA, wherein said promoter induces rhythmical expression of a gene operably linked thereto in a mammal;
(2) the isolated Period 1 promoter DNA according to (1), wherein said promoter is a rodent or human Period 1 promoter;
(3) the isolated Period 1 promoter DNA according to (2), wherein said rodent is a mouse;
(4) the isolated Period 1 promoter DNA according to (1), wherein said mammal is a rodent;
(5) a recombinant DNA comprising a Period 1 promoter and a gene operably linked to said promoter, wherein said gene is rhythmically expressed under the control of said promoter in a mammal;
(6) the recombinant DNA according to (5), wherein said Period 1 promoter is a rodent or human Period 1 promoter;
(7) the recombinant DNA according to (5), wherein said Period 1 promoter is a mouse Period 1 promoter;
(8) the recombinant DNA according to (5), wherein said gene is a luciferase gene;
(9) the recombinant DNA according to (5), wherein said mammal is a rodent;
(10) A transgenic non-human mammal wherein a gene is rhythmically expressed under the control of a Period 1 promoter DNA;
(11) the transgenic non-human mammal according to (10), wherein said gene is a reporter gene;
(12) the transgenic non-human mammal according to (11), wherein said reporter gene is a luciferase gene;
(13) The transgenic non-human mammal according to (10), wherein said mammal is a rodent;
(14) the transgenic non-human mammal according to (13), wherein said rodent is selected from the group consisting of a mouse and a rat;
(15) the transgenic non-human mammal according to (10), wherein said Period 1 promoter is a mouse or human Period 1 promoter;
(16) a progeny of the transgenic mammal according to (10);
(17) a transformant comprising a DNA as in any one of (1) to (9);
(18) the transformant according to (17), wherein said transformant is derived from a mammal as in any one of (10) to (16);
(19) a method of testing or screening a compound having an activity to modify the expression of the transgene in the transformant according to (17) comprising the steps of:
  (a) treating said transformant with said compound; and
  (b) measuring the expression of said transgene in the treated transformant;
(20) a method of testing or screening a compound having an activity to modify the expression of the transgene in the transgenic mammal according to (10) comprising the steps of:
  (a) treating said mammal with said compound; and
  (b) measuring the expression of said transgene in the treated mammal.

The present invention will be illustrated in more detail below. All publications cited herein are incorporated by reference.

1. DNAs of the Invention

The present invention provides an isolated Period 1 promoter DNA inducing rhythmical expression of a gene operably linked thereto.

Herein, "rhythmical expression" means acyclic expression based on the circadian rhythm according to which the gene expression level fluctuates.

Specifically, the present invention provides the DNA described in "P-1" to "P-4" below.

"P-1": An isolated Period 1 promoter DNA, wherein said promoter induces rhythmical expression of a gene operably linked thereto in a mammal.

"P-2": The isolated Period 1 promoter DNA according to "P-1", wherein said promoter is a rodent or human Period 1 promoter.

"P-3": The isolated Period 1 promoter DNA according to "P-2", wherein said rodent is a mouse.

"P-4": The isolated Period 1 promoter DNA according to "P-1", wherein said mammal is a rodent.

Herein, "isolated DNA" means that the DNA was separated from its natural environment. The 5' and 3'-flanking regions of the isolated DNA have been detached from their original state, or their sequences are different from the original sequences. The isolated DNA may be purified, or may be impure comprising other DNA components. Isolated DNA of the invention encompasses: DNA fragments inserted into plasmids, phages and other vectors; DNA products amplified by PCR; and, synthesized DNA. Even if the isolated DNA is returned back to its original location (for example, onto the chromosome), it would still be considered "isolated DNA".

The present invention provides an isolated Period 1 promoter DNA characterized by inducing rhythmical expression of a gene operably linked to the promoter. Herein, "Period 1 promoter" indicates a DNA having a transcription-regulating activity and deriving from the mammalian Period 1 (Per1) gene promoter. Examples of Period 1 promoters are, for example, those deriving from humans (Hida, A. et al., *Genomics,* 2000, 65, 224-233; Accession No. AB030817), monkeys, and other primates, and also from rodents including mice (Hida, A. et al., *Genomics,* 2000, 65, 224-233; Accession No. AB030818) and rats.

Period 1 promoter can be isolated from mammalian genomic DNA, for example, by screening a genomic library through hybridization using mouse or human Period 1 promoter DNA and such as a probe. An alternative method is to screen a genomic library using a partial fragment (for example, a cDNA fragment) of the coding region of Period 1 gene as a probe, and isolating its 5'-flanking region. Other than using hybridization, the Period 1 promoter can also be amplified directly from mammalian genomic DNA by the polymerase chain reaction (PCR).

"Promoter" used herein means an upstream region from the translation start site and includes the whole expression regulatory region.

DNA of the present invention can also be produced by standard methods using chemical synthesis of nucleic acids, such as the phosphoamidite method or the phosphite triester method.

The Period 1 promoter of the invention may be the whole, or a part of, the DNA comprising the wild-type Period 1 promoter, as long as it can rhythmically express a gene operably linked thereto. For example, the Period 1 promoter of the invention may comprise a fragment of 2.0 Kb or more, preferably 5.2 kb or more, more preferably 5.7 kb or more, most preferably, 6.2 kb or more, upstream of the translation initiation codon of the endogenous Period 1 gene. The DNA of this invention characterized by inducing rhythmical expression of a gene operably linked thereto, may be a DNA that is shorter than the above DNAs.

Preferably, the DNA of the invention comprises one or more E-boxes. An E-box (CACGTG) is the binding site of the CLOCK-BMAL1 complex (Gekakis, N. et al., *Science,* 1998, 280, 1564-1569). The DNA of the invention comprises preferably, three or more E-boxes, more preferably, four or more, and most preferably, five or more E-boxes. The DNA of the invention may comprise other transcription regulation elements contained in the endogenous Period 1 gene. Such transcription regulation elements generally include the cAMP responsive element (CRE), SP1 box, CAAT box, CTF/NF-1 binding site, and such, although there are no restrictions. One preferred embodiment of the DNA of the invention is a DNA comprising a spun of endogenous genomic DNA (a continuous fragment of genomic DNA) that encompasses at least three or more, more preferably four or more, even more preferably five or more E-boxes.

The promoter DNA of the invention includes those comprising an enhancer or other functional sequences, as long as the transcriptional activity is maintained. The DNA of the invention preferably comprises at least one transcription initiation site of the endogenous Period 1 promoter. Transcription initiation sites can be elucidated, for example, by analyzing a cDNA sequence obtained by 5'-RACE. These sites can also be determined by performing primer extension, and separating the resulting products using a sequencing gel (for example, 6% polyacrylamide and 8M urea gel).

The DNA of the invention preferably includes the first exon of the endogenous Period 1 gene. The DNA of the invention may also preferably comprise the first intron of endogenous Period 1 gene. The first intron of the Period 1 gene may be involved in the regulation of Period 1 gene expression. The DNA of the invention may preferably include the whole 5'-untranslated region (UTR), or a part of it, which may be contained in the second exon of the endogenous Period 1 gene. 5'-UTR contained in the exon and/or intron may comprise element(s) involved in the regulation of gene expression. The DNA of the invention may preferably comprise the translation start codon of the endogenous Period 1 gene. The DNA of the invention may include the whole open reading frame (ORF) of the Period 1 gene, or a part of it.

The DNA of the invention may also preferably include at least any one of the conserved segments identified in the upstream region of mammalian Period 1 genes. Conserved segments can be generally specified as significantly conserved regions by comparing two or more Period 1 upstream regions. Usually, conserved segments can be extracted through dot plot analysis or alignment using a computer algorithm. The genomic structure of human and mouse Period 1 gene is specifically described in Hida, A. et al. (*Genomics,* 2000, 65, 224-233; herein incorporated by reference). As previously mentioned, the nucleotide sequences of human and mouse Period 1 genes are disclosed by Accession Nos. AB030817 and AB030818, respectively. The structures of other mammalian Period 1 genes can be determined and aligned according to the above reference. One specific example of the DNA of the present invention is a DNA comprising at least one, preferably two or more, more preferably three or more, even more preferably four to six (all) of the conserved segments of the endogenous mammalian Period 1 gene specified as I, II, III, IV, V, and VI in Hida, A. et al. (*Genomics,* 2000, 65, 224-233).

A DNA construct comprising mouse-derived Period 1 promoter DNA included in the DNA of the present invention is exemplified in SEQ ID NO: 1. In this sequence, the region deriving from mouse Period 1 is from nucleotide no. 23.-no. 6787. The DNA of the invention includes a DNA comprising this region or a resembling region. This DNA has five endogenous E-box regions, a transcriptional initiation site, the first and second exons, which are split by the first intron, and a translation start codon in the second exon among the upstream regions of mouse Period 1 gene. The human Period 1 sequence corresponding to this region is from nucleotide no. 1 to no. 6573 of the human Period 1 gene sequence disclosed in Accession No. AB030817. The DNA of the invention may be a DNA comprising a sequence of this region or a resembling region of human Period 1. It is also possible to use a homologous region of some other mammalian Period 1 sequence.

Eukaryotic gene sequences often show polymorphism. One or more nucleotides may be replaced, deleted and/or inserted by such a polymorphism without affecting the essential function of the gene or gene expression. In general, activities of the promoter can be often maintained even if one or more nucleotides are modified. Therefore, the DNA of the invention includes DNA having modified nucleotides sequences compared to the mouse or human Period 1 promoter sequence exemplified above, as long as it maintains the characteristic of inducing a rhythmical expression of a gene operably linked thereto.

Period 1 promoter sequence can suitably be artificially modified. The DNA of the invention includes DNA that induces a rhythmical expression of a gene operably linked thereto, and comprises a nucleotide sequence in which one or more nucleotides in the endogenous Period 1 promoter sequence have been substituted, deleted, inserted, and/or added. Endogenous promoter sequence modifications are being routinely conducted by those skilled in the art. For example, nucleotides or elements that are not essential for inducing a rhythmical expression of a gene operably linked thereto may be deleted or replaced. Furthermore, DNA elements such as the E-box, which may be involved in the regulation of rhythmical expression, may be inserted or added. The Period 1 promoter sequence may be combined with other promoter sequence(s) to make a heterologous promoter, fusion-promoter or chimeric-promoter. The other promoter combined is not restricted. Promotors modified in such a manner are also included in the "Period 1 promoter" of the invention.

The DNA of the invention also includes a DNA comprising a DNA hybridizing to the DNA comprising the sequence from nucleotide no.23 to no. 6787 of SEQ ID NO: 1, the DNA being able to induce a rhythmical expression of a gene operably linked thereto. Hybridization condition can be suitably selected. The hybridization can be done, for example, in a mixture consisting of 6x SSPE, 5x Denhardt's solution, 0.5% SDS, 100 µg/ml denatured salmon sperm DNA, and 50% formamide, usually at 42° C., less stringently at 32° C., or more stringently at 65° C.

Whether or not the DNA of the invention is rhythmically expressed can be confirmed by detecting whether the gene operably linked to the downstream of the DNA can be rhythmically expressed in compliance with the circadian rhythm when the gene is placed in a cell within a mammal having a circadian rhythm. For example, the DNA expression is temporally detected in a mammal having cells into which the DNA of the invention has been introduced. Alternatively, cells within the body could be taken out to observe the expression. To give an example, a mammal having cells or tissues comprising the DNA of the invention within its body, is raised under a normal light cycle (for example, LD 12:12) for a certain time period (for example, one week) or more. Then, the cells or tissues are taken out, and the present DNA expression is periodically detected starting from immediately after the cells or tissues are taken out. The detection is conducted, for example, in constant darkness (DD). If these detections show that the rhythmical expression of the downstream gene is induced by the DNA focused on, then, it can be said that the DNA induces a rhythmical expression. The mammal used in the detection is not especially restricted, but rodents are suitable. More specifically, mice or rats are used. Examples are conventional Wistar rats or C57/B6 mice. The rhythmical expression induced by the DNA of the invention can be verified by fluctuations of expression in compliance with the circadian rhythm. Under optimum conditions, the DNA of the invention induces at least one cycle (one day) or more, preferably two cycles (two days) or more, more preferably three cycles (three days) or more, and even more preferably four cycles (four days) or more (e.g. one to two weeks or more) of rhythmical expression of downstream genes even in constant darkness (DD). The continuation of rhythmical expression may change according to assay conditions and tissues.

The DNA of the invention may be comprised within vector DNA. It may also take the form of RNA as an intermediate. For example, the DNA (or RNA) of the invention may be included in a plasmid, cosmid, phagemid, phage, artificial chromosome including YAC and BAC, virus including retrovirus, lentivirus, and adeno-associated virus (AAV), or transposable element, and such. A selection marker gene (e.g., antibiotics resistant gene) may be linked to the DNA of the invention, according to needs.

In summary, the DNA of the invention is useful in inducing a rhythmical expression of a gene operably linked thereto in a mammal. The DNA of the invention is an isolated Period 1 promoter DNA characterized by inducing rhythmical expression of a gene operably linked thereto in a mammal. Furthermore, the present invention relates to the use of the above-described DNA of the invention for inducing a rhythmical expression of a gene operably linked thereto. The present invention also relates to the use of the above-described DNA of the invention for detecting rhythmical expression of a gene operably linked thereto.

The present invention provides a recombinant DNA comprising Period 1 promoter and a gene operably linked to the downstream thereof, wherein the gene is rhythmically expressed under the control of said Period 1 promoter in a mammal. Such genes include those in which a gene is operably linked to the downstream of the above-described Period 1 promoter DNA of the present invention. Specifically, the DNAs described in "G-1" to "G-4" below are included in the present invention.

"G-1": A recombinant DNA comprising a Period 1 promoter and a gene operably linked thereto, wherein said gene is rhythmically expressed under the control of said promoter in a mammal.

"G-2": The recombinant DNA according to "G-1", wherein said Period 1 promoter is a rodent or human Period 1 promoter.

"G-3": The recombinant DNA according to "G-1", wherein said Period 1 promoter is a mouse Period 1 promoter.

"G-4": The recombinant DNA according to "G-1", wherein said gene is a luciferase gene.

"G-5": The recombinant DNA according to "G-1", wherein said mammal is a rodent.

Herein, a "recombinant DNA" is that which is linked in a way different to the natural state. "Recombinant DNA" can be produced by genetic engineering. DNA comprising isolated DNA is included in a "recombinant DNA".

Herein, "operably linked" means that the gene is linked in such a manner that it is expressed under the control of the promoter. In the DNA of the invention, the gene operably linked to the Period 1 promoter is rhythmically expressed under the regulation of the promoter. Such a rhythmical expression typically occurs when the DNA is introduced into cells within mammals having a circadian rhythm. A nucleotide sequence of any length can be inserted between the promoter and the gene whose expression is controlled by the promoter as long as the sequence does not affect the rhythmical expression of the gene induced by the promoter. The gene whose expression is controlled by the promoter is linked preferably downstream, more preferably immediately downstream of the promoter.

The gene linked is not especially restricted, and any gene can be used. For example, the gene may be encoding a desired protein, such as a structural protein, a marker protein, an enzyme, a receptor, a channel, a membrane protein, a hormone, a cytokine, a growth factor, a ligand, or some other physiological factor. The DNA of the invention may comprise one or a plurality of genes. The gene may be a natural gene, or may be an artificially modified or constructed gene. The desired gene can be rhythmically expressed in compliance with the circadian rhythm, by placing the DNA of the invention comprising the linked gene in a cell within a multicellular organism having a circadian rhythm. In one preferred embodiment of the invention, a reporter gene is linked to the downstream of the Period 1 promoter. Such DNAs are useful in detecting the circadian rhythm in vivo or within tissues.

The reporter gene used is not restricted as long as its expression can be detected. Reporter gene expression can be directly or indirectly detected through detecting transcripts, translational products, or the activity or function(s) of translational products. Any well-known reporter gene can be used as the reporter gene. Examples are, the chloramphenicol acetyltransferase gene, β-D-glucronidase gene, β-D-galactosidase gene, luciferase gene, aequorin gene, green fluorescent protein (GFP) gene, and so on. In the present invention, it is preferable that the reporter gene be such that its expression can be detected without invading the cell. Preferable is a reporter gene in which the expression can be detected with a high sensitivity, and in which the turn over of expression products are rapid to a degree that facilitates the distinction between expressional temporal patterns. One appropriate example is the luciferase gene. Luciferase assay allows real-time detection of gene expression in viable cells, tissues, organs and even in individuals.

Any of the above-described Period 1 promoter DNAs can be used as the Period 1 promoter DNA linked to the gene. As long as the gene is rhythmically expressed, the wild-type Period 1 promoter or a partial fragment thereof may be used. A reporter gene construct comprising the mouse-derived Period 1 promoter included in the DNA of the present invention is exemplified in SEQ ID NO: 1. In this sequence, the mouse Period 1-derived region is from nucleotide number 23 to 6787. Other than using mouse-derived Period 1 promoter DNA, the above-described human or some other mammalian Period 1-derived DNA can also be used as Period 1 promoter DNA. Period 1 promoter DNA may comprise modified sequence(s) as well. When the Period 1 gene-derived promoter DNA comprises the ORF encoding the Period 1 protein, or a part of it, the gene linked to the downstream of the Period 1 promoter DNA can be linked with this ORF in frame, and expressed as a fusion protein. Alternatively, the gene maybe independently expressed.

In the DNA comprising a gene linked to the Period 1 promoter DNA, the gene comprised in the DNA is rhythmically expressed in compliance with the circadian rhythm, in cells within a mammal having a circadian rhythm. Whether or not the gene is rhythmically expressed can be confirmed by periodically detecting the gene expression within or outside the body of a mammal, as earlier described.

The DNA of the invention comprising a gene may be included within vector DNA. It may also take the form of RNA as an intermediate. For example, these DNA (or RNA) may be included in a plasmid, cosmid, phagemid, phage, artificial chromosome including YAC and BAC, virus including retrovirus, lentivirus, and adeno-associated virus (AAV), or transposable element, and such. A selection marker gene (e.g., antibiotics resistant gene) may be linked to the DNA of the invention, according to needs.

In summary, the recombinant DNA of the invention comprising a gene is useful in inducing a rhythmical expression of the gene in a mammal. The DNA of the invention relates to a recombinant DNA comprising a gene operably linked to a Period 1 promoter, in which the gene is rhythmically expressed under the control of the Period 1 promoter in a mammal. The DNA can be a Period 1 promoter DNA construct for inducing a rhythmical expression of a gene operably linked thereto. The present invention relates to the use of the above DNA of the invention that comprises a gene in inducing a rhythmical expression of the gene. The present invention also relates to the use of the above DNA of the invention that comprises a gene in detecting rhythmical expression of the gene.

2. Transformants carrying the DNA of the invention

The present invention provides transformants carrying the DNA of the invention. The transformant used is not restricted as long as it comprises the DNA of the invention, and examples include cells, tissues, organs, individuals, and such. As long as the DNA of the invention is carried, transformants include prokaryotes and eukaryotes such as bacteria, yeasts, mammals, plants, insects, and so on. In one preferred embodiment, the DNA of the invention uses a cell derived from a multi-cellular eukaryote having the circadian rhythm as a host. More preferably, a mammalian cell is used as a host. Examples of mammals include, humans, monkeys, mice, rats, hamsters, dogs, cats, cattle, pigs, and such, but are not restricted to these. Mammalian cells carrying the DNA of the invention can rhythmically express this DNA in compliance with the circadian rhythm when transplanted within the mammalian body. The form of the host cell used in the invention is not restricted. It may be in a free form such as floating cells, or may be forming a tissue or an organ. It may also be an individual. Host cells include fertilized eggs, early stage-embryos, embryonic stem (ES) cells, and such as well. These cells are useful in the preparation of transgenic mammals described later on. Tissues or cells deriving from transgenic mammals are also included in the transformants of the invention. These tissues or cells could be primary cultures, passaged cultures thereof, or established cell lines. Transgenic mammals themselves are included in the transformants.

Well-known transfection methods can be used to introduce the DNA of the invention into host cells. For example, the calcium phosphate co-precipitation procedures, DEAE-dextran methods, electroporation, lipofection, microinjection and such are used to introduce DNA into mammalian cells. DNA may be introduced by infection via viruses. The host cells may be those that transiently or stably carry the DNA of the invention. Preferably, the DNA of the invention is integrated into a chromosome of the host cell. The host cell may carry one or more copies of the DNA of the invention. A high number of integrated copies is thought to be preferable because it results in a stronger expression in reporter assays. For example, the transformant cell of the invention may carry, per diploid genome, around three or more copies, preferably around four or more copies, and more preferably around five or more copies of the DNA of the invention. The copy number can be estimated by southern blot analysis using the DNA of the invention as the probe.

3. Transgenic mammals

The present invention provides a transgenic non-human mammal wherein a gene is rhythmically expressed under the control of a Period 1 promoter.

Specifically, the following transgenic non-human mammals from "Tg-1" to "Tg-7" are provided.

"Tg-1": A transgenic non-human mammal wherein a gene is rhythmically expressed under the control of a Period 1 promoter DNA of any one of the above-mentioned "P-1" to "P-4".

"Tg-2": The transgenic non-human mammal according to "Tg-1", wherein said gene is a reporter gene.

"Tg-3": The transgenic non-human mammal according to "Tg-1", wherein said reporter gene is a luciferase gene.

"Tg-4": The transgenic non-human mammal according to "Tg-1", wherein said mammal is a rodent.

"Tg-5": The transgenic non-human mammal according to "Tg-1", wherein said rodent is selected from the group of a mouse and a rat.

"Tg-6": The transgenic non-human mammal according to "Tg-1", wherein said Period 1 promoter is a mouse or human Period 1 promoter.

"Tg-7": A progeny of the mammal according to "Tg-1".

The mammals below are included in the above-described transgenic mammals.

"Tg-8": A transgenic non-human mammal carrying the DNA of any one of the above-mentioned "G-1" to "G-5", wherein the transgene is rhythmically expressed under the control of said Period 1 promoter.

"Tg-9": The transgenic non-human mammal according to "Tg-8", wherein said gene is a reporter gene.

"Tg-10": The transgenic non-human mammal according to "Tg-8", wherein said reporter gene is a luciferase gene.

"Tg-11": The transgenic non-human mammal according to "Tg-8", wherein said mammal is a rodent.

"Tg-12": The transgenic non-human mammal according to "Tg-8", wherein said rodent is selected from the group consisting of a mouse and a rat.

"Tg-13": The transgenic non-human mammal according to "Tg-8", wherein said Period 1 promoter is a mouse or human Period 1 promoter.

"Tg-14": A progeny of the mammal according to "Tg-8".

Transgenic mammals such as these can be prepared by introducing the abovementioned DNA of the invention. In the transgenic mammals of the invention, the introduced gene may show a constitutive rhythmical expression, or is normally not expressed, but is rhythmically expressed only after the expression is induced. This expression may be triggered, for example, by exogenous stimuli or environmental changes. Such expression systems can be achieved by, for example, using the Cre-loxP system. Alternatively, the use of a chimeric promoter with another inducible promoter is also envisaged. The expression may be systemic, or may be specific to a cell, tissue, or organ.

The transgenic mammals can be prepared following well-known methods, and the method used is not especially restricted. For example, a fertilized egg is collected, and a gene is injected into the male pronucleus of the egg by microinjection using an injection pipette. Alternatively, the DNA of the invention is introduced into an embryonic stem (ES) cell, and selected ES cells are injected into a fertilized egg (blastocyst) by microinjection. Animals whose oviduct the eggs are returned into are prepared (pseudopregnant females, etc.), and about 10 to 15 eggs are transplanted in each individual.

Introduction of the transgene into founders (progenies) are confirmed by extracting genomic DNA from the tip of the tail and detecting the transgene by Southern hybridization or PCR methods. Expression of the transgene can be detected by appropriate methods according to the transgene. Transcripts of the transgene can be detected by Northern hybridization or RT-PCR methods. Detection by the Western blotting method is also possible using an antibody specific to a protein. Heterogenic transgenic mammals can be obtained by crossing chimeric animals into whose germ line the genes have been introduced with the normal animals. Homogenic transgenic mammals can be obtained by crossing heterogenic transgenic mammals with each other. The transgenic mammals of the invention include these progenies as well.

The non-human mammals of the invention are rodents such as mice, rats, hamsters, and guinea pigs, and also, rabbits, pigs, goats, sheep, horses as well as cattle, and such. Rodents are preferable as the animals of the invention, and especially, mice or rats are preferable.

The Examples describe a transgenic mouse and rat into which a DNA comprising a luciferase gene as the reporter gene linked to the downstream of a Period 1 promoter has been introduced. By using the transgenic mammal of the invention, which expresses luciferase as the reporter, it is possible to detect the temporal change of transcription real-time by detecting luciferase activity in the desired tissue. Light emission from cultured suprachiasmatic nuclei (SCN) of transgenic rodents was invariably and robustly rhythmic. Remarkably, the rhythm from rat SCN culture persisted for up to 32 days in vitro. These results directly prove that the DNA of the invention itself is sufficient enough to induce a gene expression compliant to the circadian rhythm.

Surprisingly, the circadian oscillation of the reporter gene expression was evidently observed in all the peripheral tissues examined. The transgenic mammal of the invention is preferably a transgenic non-human mammal in which the transgene is rhythmically expressed in a peripheral tissue. The peripheral tissue includes the liver, lung and skeletal muscle, but is not restricted to these. These peripheral tissues showed circadian rhythms of light output that phase-lagged the SCN rhythm by 7-12 hours. The lagged-pattern of peripheral tissue expression against SCN is thought to reflect the normal coordination of the biorhythm of the complex mammal made of multi-organs. The transgenic mammals of the invention are also useful in detecting the circadian rhythm in peripheral tissues.

Specifically, the transgenic mammals of the present invention are useful for investigating the function and expression control of Period 1, clarifying mechanisms of jet lag or sleep disorder relating to circadian rhythmicity, and developing mammal models used for screening and testing compounds useful for treatment of circadian rhythm disorders.

4. Assay and Screening

Various testings or screenings can be done using the transformants or transgenic mammals comprising the DNA of the invention that expresses a reporter gene. Effects of stimuli or compounds that regulate the reporter gene expression can be evaluated or these can be screened by detecting the reporter gene expression in these tissues or cells under various arbitrary conditions. Stimulations include temperature, light, motion, and other shocks. The compound used is not restricted. The present invention specifically relates to a method of testing or screening a compound that modifies the expression induced by the Period 1 promoter introduced into the transformants or transgenic mammals of the invention using the transformants or the transgenic mammals.

The methods described in "M-1" and "M-2" below can be given as the testing or screening methods of the invention.

"M-1": A method of testing or screening a compound that has activity of modifying the expression of the transgene in the transformant of the present invention comprising:
  (a) treating said transformant with said compound; and
  (b) measuring the expression of said transgene in the treated transformant.

"M-2": A method of testing or screening a compound that has activity of modifying the expression of the transgene in the mammal of the present invention comprising:
  (a) treating said mammal with said compound; and
  (b) measuring the expression of said transgene in the treated mammal.

The methods of the invention are useful in screening a compound that regulates Period 1 gene expression. The methods are also useful in the screening of pharmaceutical drugs targeting circadian rhythm disorders. Especially, the screening method given below is enabled by the present invention.

A method of testing or screening a pharmaceutical drug useful for treating circadian rhythm sleep disorder comprising:
  (a) treating the transformant or the transgenic non-human mammal of the present invention with the pharmaceutical drug; and
  (b) measuring the expression of the reporter gene in the treated transformant or mammal.

The compound used in the testing or screening method of the invention is not especially restricted. Examples include, inorganic compounds, organic compounds, peptides, proteins, natural or synthetic low-molecular-weight compounds, natural or synthetic high-molecular-weight compounds, tissue or cell extracts, culture supernatants of microorganisms, plant or marine organism-derived natural components, and such, but are not restricted thereto. Expression products of gene libraries, or expression cDNA libraries, and such may also be used. The method of treating with the compound is not especially restricted. In vitro treatment can be implemented by contacting cells with the compound, for example by adding the compound into culture media, introducing the compound into cells using microinjection or transfection reagents, and such. In vivo treating methods include those methods well known to skilled artisans such as arterial, intravenous, subcutaneous, or intraperitoneal injections; oral, enteral, intramuscular, or intranasal administrations; administration to eyes; intracerebral, intracerebroventricular administrations or administration to peripheral organs via an injection or a catheter; and such methods. The compound is administered as a suitable composition. For example, it can be mixed with water, physiological saline, buffers, salt, stabilizers, preservatives, suspensions, and such.

The reporter gene expression can be assayed while the mammals or the cells are still a live or after lysing the cells.

For example, to assay luciferase gene expression in living tissues, the bioluminescence can be continuously measured by a photo multiplier detector as shown in the Example or by some other similar detector described in "Yamazaki, S. et al., *Science*, 2000, 288, 682-685" herein incorporated by reference. Luciferase activities in lysed tissues or cells can be assayed, for example, with the Dual-Luciferase Reporter Assay System (Promega), and such. Reporter gene expression can be assayed temporally or spatially. The expression can also be analyzed by detecting the phase, amplitude, and/or period of the expression rhythm. The method of the invention enables the evaluation of the immediate or prolonged effects (including phase changes) of compounds. If the compound administration modifies these expressions, the compound becomes a drug candidate for regulating Period 1 gene expression. Such a compound is anticipated to be applied as a pharmaceutical drug for various circadian rhythm disorders including sleep disorders. For example, drugs that reset or initiate the oscillation of reporter gene expression, are anticipated to delay or advance the phase of the pacemaker. Therefore, these drugs can be used to lead the desynchronized expression pattern to its normal synchronization. A pharmaceutical drug screened by the present invention is administered to the transgenic mammals of the invention, which is induced to be a circadian rhythm disorder model, to estimate the therapeutic effect of the drug.

When detecting gene expression in a transgenic mammal, the assayed organ is not especially restricted, and includes, the central and peripheral nervous systems (CNS and PNS) including SCN of the hypothalamus, and other peripheral tissues including, but not limited to, the liver, lung, and skeletal muscles. The system disclosed in the present invention is useful to evaluate the phase relationship and synchronization mechanism of Period 1 expression in the SCN and peripheral tissues.

The system of the present invention can be used to identify many putative factors that regulate Period 1 expression. If novel in vivo factors and genes relating to circadian rhythm are identified using this system, the in vivo oscillation of these factors and gene expressions can be determined. Thereby, factors controlling the oscillation phase of SCN and peripheral tissues can be isolated. These are thought to be novel genes and proteins involved in the circadian rhythm, and using these as targets, the screening of novel drugs will become possible. Such a screening can be done both in vivo and in vitro.

Specifically, an in vivo screening method using the transgenic mammal of the invention comprises the steps of:
 (a) administering a compound to a transgenic mammal whose circadian rhythm has already been determined;
 (b) periodically detecting the expression level of the reporter gene in the transgenic mammal and verifying the expression rhythm;
 (c) comparing the reporter gene expression rhythm following the administration of the compound to that prior to administration; and,
 (d) selecting a compound that modifies the phase, period, or amplitude of the expression rhythm.

The reporter gene expression rhythm can be detected by the method in which the reporter gene expression rhythm is detected within living animals; the method in which the variation of expression is continuously observed by culturing excised tissues; or the method of periodically preparing extracts of animal tissues and detecting the expression level at each point For example, luciferin is given to a transgenic animal at an appropriate timing by a suitable method (for example, intravenous injection, intraperitoneal administration, intracerebroventricular administration, and such). The animal is then anesthetized, and the reporter gene-expressing site, and expression level are determined by counting the luciferase luminescence by a CCD camera. This measurement is done a few times every few hours to establish the expression rhythm of the individual animal (see Sweeney T. J. et al., Visualizing the kinetics of tumor-cell clearance in living animals, *PNAS* 1999, 96, 12044-12049; and, Contag P. R. et al., Bioluminescent indicators in living mammals, *Nature Medicine*, 1998, 4, 245-247).

As mentioned earlier, novel drugs can be screened in vitro as well, using the present invention. Such an in vitro screening method comprises the steps of:
 (a) culturing the transformant of the present invention or a tissue or cells derived from the transgenic mammal of the present invention;
 (b) treating the transformant or tissue or cells with a compound for an appropriate period of time, and then continuing the culture;
 (c) periodically detecting reporter gene expression level; and,
 (d) selecting a compound that modifies the reporter gene expression rhythm (phase, period, and amplitude) following the treatment in (b).

Herein, the tissue or cells derived from the transgenic mammal of the present invention may be cells of primary culture or an established cell line. The tissue, cells, and such used herein are not restricted, although the SCN, subthalamic marginal cells, peripheral nerves, and such are preferred. The treatment with the compound can be performed by, for example, immersing the tissue, cells, and so on in a solvent to which the compound had been added, for a specific period of time. When measuring the change in reporter gene expression rhythm, the comparison can be done using identical tissues or cells whose expression rhythm has been determined beforehand, or using control tissues or cells, and such that have not been treated with the compound.

In the above-mentioned in vivo and in vitro screening methods, a stimulatory treatment such as light stimulation may be done together with the administration or treatment with the compound.

A compound identified by the testing or screening method of the invention can be used as a pharmaceutical drug against desired circadian rhythm diseases or disorders. These drugs can be prepared as a pharmaceutical composition by combining suitable pharmaceutically acceptable carriers, solutes, and solvents. The drugs can be applied for diseases or disorders such as jet lag symptoms, shift-work sleep disorder, delayed sleep phase syndrome, and irregular sleep-wake disorder.

When using a compound isolated by the screening method of the invention as a pharmaceutical drug, it can be directly administered to the patient or it can be formulated into a pharmaceutical composition prepared by well-known pharmaceutical preparation methods. For example, it can be administered after suitably combining with a pharmacologically acceptable carrier or medium, specifically, sterilized water, physiological saline, plant oils, emulsifiers, suspensions, and such. The pharmaceutical compositions of the invention can take the form of aqueous solutions, tablets, capsules, troches, buccal tablets, elixirs, suspensions, syrups, nasal drops, inhalants, and such. Compound's contents may be suitably determined. These can be given to the patient, for example, usually through arterial, intravenous, or subcutaneous injection, or oral administration, and such methods well known to skilled artisans. The dosage given varies according to the body-weight, age, administration method and symptoms of a patient, but a skilled artisan can suitably select the dosage amount. Generally, the dosage amount varies depending on the effective concentration within blood and metabolic duration of the drug, but the maintenance dose per day is thought to be around 0.001 mg/kg to 1 g/kg, preferably 0.01 mg/kg to 100 mg/kg, and more preferably, 0.1 mg/kg to 10 mg/kg. The administration can be done once to several times per day. If the compound can be encoded by a DNA, the DNA can be incorporated into a gene therapy vector to conduct gene therapy.

BEST MODE FOR CARRYING BUT THE INVENTION

The present invention will be illustrated with reference to the following examples, but is not construed as being limited thereto.

EXAMPLE 1

Construction of Transgenic Rat

Figure 1:
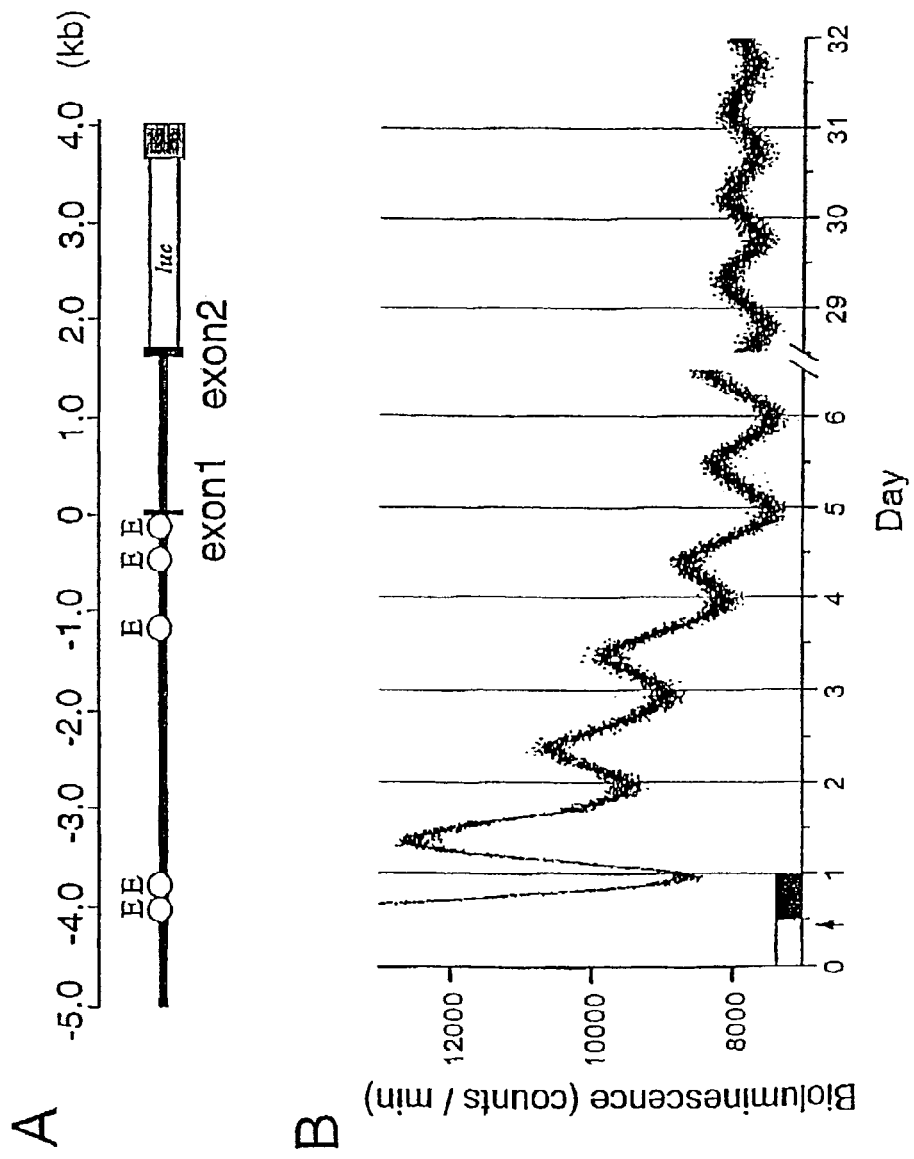
FIG. 1(A) shows a diagram of the mouse Per1-luc transgene. Heavy line indicates the mPer1 fragment, while the open bar and the shaded box indicate the positions of the luciferase gene and polyadenylation fragments, respectively. The circles represent E-boxes.
FIG. 1(B) shows a representative circadian rhythm of bioluminescence from a cultured SCN explanted from a Per1-luc transgenic rat. Black and white bars show the animal's previous light:dark conditions. The explant was made just before lights-off (arrow) and luminescence was monitored immediately. The near 24-h rhythm peaked in the middle of the subjective day and persisted for 32 days in vitro, at which time the culture was removed from the assay. Rhythmicity persisted for more than 2 weeks in the several SCN cultures that were maintained for this duration. Similar rhythmicity of lower intensity was found in a separate line of Per1-luc transgenic rats "W(per1)5". In that line, the SCN rhythm also peaked in the middle of the subjective day and persisted for 28 days in vitro.

The present inventors constructed a new transgenic rat model in which the mouse Per1 gene promoter is linked to a luciferase reporter (FIG. 1A).

A mouse Per1 genomic fragment of 6.7 kb was linked directly to the second codon of the firefly luciferase cDNA flanked by the polyadenylation sequences of the SV40 late gene. The mPer1 fragment includes five functional E-box regions, a transcription initiation site, the first and second exons that are split by the first intron, and a translational start codon in the second exon (FIG. 1A). As expected, the reporter gene was induced by the concerted action of Clock and B mall, and repressed by either Cry1 or Cry2 in a transient co-transfection assay "A. Hida et al., data not shown; see *Genomics,* 2000, 65, 224 to 233". The linearized reporter fragment was microinjected into 302 fertilized eggs of Wistar rats (Charles River Japan Inc. ) "S. Hoshi, T. Ninomiya, M. Homma, A. Yuki, Anim. *Biotechnol.,* 1990, 1, 175". Transgenic rats were identified by PCR and the copy number of the transgene was determined by a Southern analysis. Six transgenic rats (5 male and 1 female) were obtained by the screening of 60 weaned pups. All of the 6 founder rats developed normally, although two of these were sterile or mosaic, respectively. Luciferase activity in brain extracts of the 4 transgenic lines was roughly proportional to the copy number of the reporter gene. A transgenic line "designated as W(per1) 1", which showed circadian oscillation of luciferase activity in the SCN, was selected for further study. There are approximately 12 copies/genome of the transgene integrated in W(per1)1, and the luciferase activity in the brain is 1431 relative luminescence units (Turner Designs)/mg protein.

For both male Per1-luc and male wild type controls, the period of the wheel running activity rhythm in constant darkness was measured. The period of the transgenic rats (measured at 8 to 10 weeks of age) was 24.43±0.02 hours (SEM, n=20). That is very close to the period of the wild type mammals (24.33±0.01 hours, n=26), measured at 6 to 8 weeks of age, indicating that the transgene does not disrupt molecular circadian time keeping.

EXAMPLE 2

Preparation of Rat Tissues

The resulting Per1-luc rats were raised in light:dark (LD) 12:12 cycles and cultured several light-emitting tissues in constant darkness and constant temperature (36° C.). Explants of SCN, skeletal muscle, liver, and lung were cultured under static conditions (i.e. without changing the medium) 30 to 60 minutes prior to light offset, transgenic rats were anesthetized with Halothane and decapitated. The brain was removed and placed in chilled Hanks buffered saline solution. The paired SCN were explanted from 400 pm coronal sections of brains from transgenic rats made with a Vibroslicer and placed on a culture membrane (Millicell-CM, PICM030-50; Millipore). The membrane and explant were placed in a petri dish covered with a glass plate and sealed with silicone grease. SCN were cultured in 35 mm petri dish with 1.2 ml culture medium serum-free, low sodium bicarbonate, no phenol red, Dulbecco's Modified Eagle's Medium (13000-021, GIBCO BRL)] supplemented with 10 mM HEPES (pH 7.2), B27 (2%; 17504-010, GIBCO BRL), and 0.1 mM luciferin (beetle luciferin, potassium salt, Promega) and antibiotics (25 U/ml Penicillin, 25 µg/ml Streptomycin) "M. E. Geusz, et al., *Current Biology*, 1997, 7, 758". Muscle, liver and lung were dissected with a pair of scalpels to sections of about 1 mm thickness and 1-2 mm square and cultured in the same way as above without the Millicell membrane. The cultures were done in constant darkness and constant temperature (36±0.2° C.), and the light output was measured continuously from individual cultures using a Hamamatsu photomultiplier tube detector assembly. Bioluminescence was measured with photo multiplier tube (PMT) detector assemblies (HC135-11 MOD Hamamatsu), modified from HC135-01. PMTs (R3550) were specially selected with dark counts below 20 counts per sec at room temperature and the Pre-scale factor was reduced to 2. The modules and cultures were maintained in a light-tight water-jacketed incubator at 36° C. and interfaced to IBM PC type computers for continuous data acquisition. The PMT was positioned about 2 cm above the culture and photon counts were done through the glass cover slip-and integrated over 1 min intervals. Dark counts (nonspecific counts) from the PMTs were about 20-40 per sec at 36° C. (M. E. Geusz, et al., *Current Biology*, 1997, 7, 758).

EXAMPLE 3

Construction of Transgenic Mice

A transgenic mouse line was constructed in which luciferase is rhythmically expressed under the control of the mouse Per1 promoter, using methods similar to constructing the above described transgenic rat line.

A mouse Per1 genomic fragment of 6.7 kb was linked directly to the second codon of the firefly luciferase cDNA flanked by the polyadenylation sequences of the SV40 late gene. The mPer1 fragment includes five functional E-box regions, a transcription initiation site, the first and second exons that are split by the first intron, and a translational start codon in the second exon. As expected, the reporter gene was induced by the concerted action of Clock and B mall, and repressed by either Cry1 or Cry2 in a transient co-transfection assay. The linearized reporter fragment was microinjected into 63 fertilized eggs of C57/B6 mice. Transgenic mice were identified by PCR and the copy number of the transgene was determined by a Southern analysis. A transgenic mouse line was obtained by the screening of 8 weaned pups. The transgenic mouse (designated as L1) developed normally, and showed circadian oscillation of luciferase activity in the SCN. There are approximately 6 copies/genome of the transgene integrated in L1, and the luciferase activity in the brain is 552 relative luminescence units (Turner Designs) per mg protein.

EXAMPLE 4

Preparation of Rat SCN 30 to 60 minutes prior to light offset, transgenic mouse was anesthetized with Halothane and decapitated. The brain was removed and placed in chilled Hanks buffered saline solution. The paired SCN were explanted from 400 µm coronal sections made with a Vibroslicer and placed on a culture membrane (Millicell-CM, PICM030-50; Millipore). The membrane and explant were placed in a petri dish covered with a glass plate and sealed with silicone grease. SCN were cultured in 35 mm petri dish with 1.2 ml culture medium "serum-free, low sodium bicarbonate, no phenol red, Dulbecco's Modified Eagle's Medium (13000-021, GIBCO BRL)] supplemented with 10 mM HEPES (pH 7.2), B27 (2%; 17504-010, GIBCO BRL), and 0.1 mM luciferin (beetle luciferin, potassium salt, Promega) and antibiotics (25 U/ml Penicillin, 25 µg/ml Streptomycin). Bioluminescence was measured with photo multiplier tube (PMT) detector assemblies (HC135-11MOD Hamamatsu), modified from HC135-01. The modules and cultures were maintained in a light-tight water-jacketed incubator at 36° C. and interfaced to IBM PC type computers for continuous data acquisition.

EXAMPLE 5

Detection of Rhythms of SCN and Periphery

Figure 2:
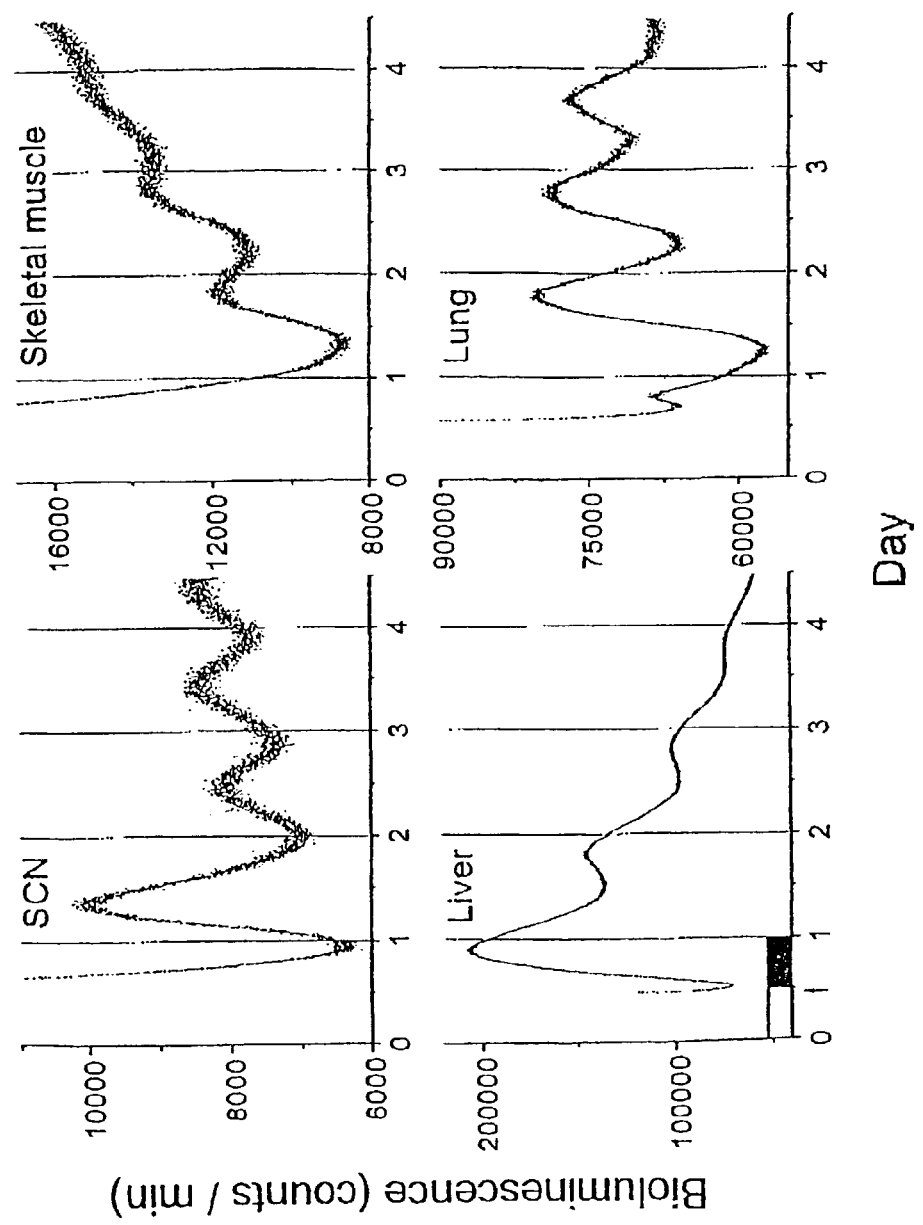
FIG. 2 shows circadian rhythms expressed in vitro from several tissues from the same animal "W(per1)1". Various tissues from the same animal express circadian rhythms with different phase relationships. The tissues were explanted just before lights-off (arrow). The SCN showed a clear circadian rhythm with its peak in the middle of the subjective day, while rhythms from skeletal muscle, liver and lung all peaked around the middle of the subjective night. Rhythms in muscle, liver, and lung always damped after 2-6 cycles.

Light emission from the SCN was invariably and robustly rhythmic (N=48), indicating that the engineered mPer1-luc transgene was being rhythmically transcribed under the control of normal circadian mechanisms. Remarkably, the SCN rhythm persisted for up to 32 days in static culture (FIG. 1B). Preliminary data (not shown) from mammals sacrificed 3 or 9 hours before lights-off indicates that these times of sacrifice does not affect the phase of the SCN rhythms. Liver, lung and skeletal muscle all showed circadian rhythms of light output which phase-lagged the SCN rhythm by 7-12 hours. This phase difference between the SCN and peripheral tissues is similar to the phase-lag observed in vivo (M. J. Zylka et al., *Neuron*, 1998, 20, 1106). Importantly, these rhythms were not as robust as those recorded from the SCN and always damped out after between 2 and 6 cycles in culture (FIG. 2).

EXAMPLE 6

Effect of Phase Advance and Delay

The light cycle was advanced or delayed by 6 hours, a treatment roughly similar to a rapid trans-Atlantic flight in either direction. The phase advance was accomplished by advancing the light onset; the phase delay was accomplished by delaying the light offset.

Heterozygous transgenic rats were raised under light:dark (LD) 12:12 cycles. Mother and pups were group housed until sacrificed. Cages containing mother and pups were moved to light controlled boxes with either 6 hours advanced or 6 hours delayed light:dark cycles. Light was produced by a 40 W florescent lamp (F40CW/RS/EW, Philips) located about 35 cm above the bottom of the cage. The light intensity was 30-60 W/cm$^2$ corresponding to about 100-200 lux at cage level. At the time of sacrifice, mammals were 15-41 days old. Both male and female mammals were used and no differences due to sex were observed.

Figure 3:
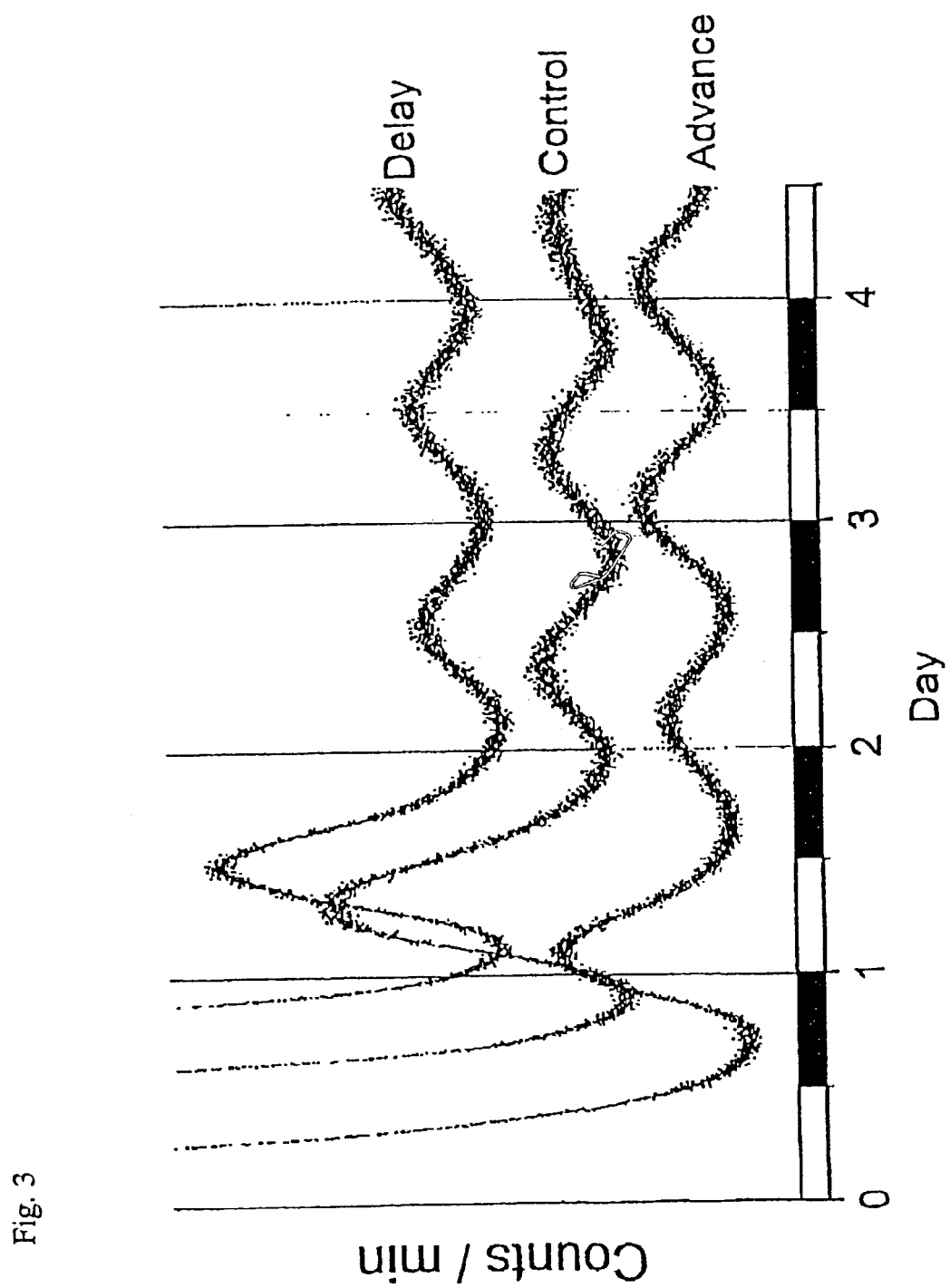
FIG. 3 shows the re-entrainment in SCN oscillator in phase-advanced and phase-delayed light cycles. In vivo light:dark history determines the phase of circadian Per1-luc expression in cultured SCN. Bioluminescence from SCN taken from unshifted (control), advanced and delayed mammals are plotted against the original light and dark cycle (0 is the time lights were turned on before the phase shifts). A continuation of that original light cycle has been diagrammed at the bottom of the figure. The x-axis is in "counts/min", however, the traces have been shifted vertically for clarity.
Figure 4:
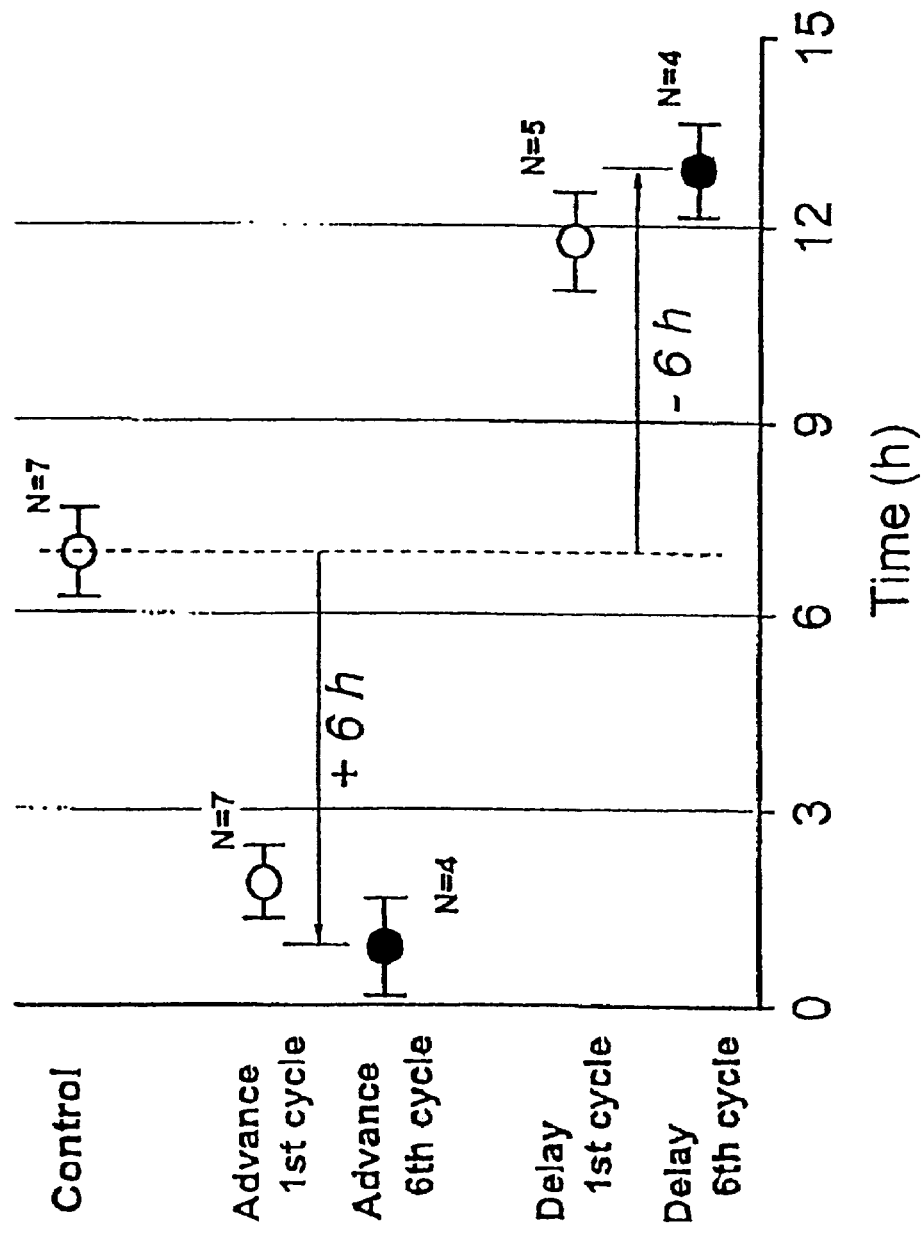
FIG. 4 shows the rapid re-entrainment following 6-hour delays and advances of the light cycle in SCN. Average time of peak of the SCN circadian rhythm of unshifted control and of SCN rhythms from mammals following either a 6 h advance (+) or delay (−) of the light cycle. The first peak in culture was used for determining the time of the peak, which was done by detecting the time at the highest point in each cycle. The average time of peak on the 1st (open circle) and 6th (filled circle) full cycle following the shift are shown (bar indicates±SEM). Number of mammals is indicated beside each circle. Preliminary data (not shown) from mammals sacrificed 3 or 9 hours before lights-off indicates these times of sacrifice does not affect the phase of the SCN rhythms.

The mammals were sacrificed 1 or 6 cycles after the phase shift of the light cycle and the SCN was cultured to determine the degree to which it has shifted. The rhythm in the SCN shifted rapidly and clearly in all the mammals and was almost fully shifted 1 cycle after the shift of the light cycle in either direction. Six cycles after the shifts, the SCN rhythms had completely regained their steady state relationship with the light cycle. There was no noticeable effect of the light cycle shifts on the amplitude of SCN rhythmicity (FIG. 3 and 4).

EXAMPLE 7

Effect of Phase Advance and Delay to Intact Rats

We applied the same phase shift paradigm to intact rats and recorded locomotor activity rhythms before and after the light cycle shift.

Male heterozygous transgenic rats were weaned and transferred to individual running wheel cages at 4 weeks of age. They were maintained in the same light:dark conditions to which they had been previously exposed. Two days after transfer, mammals were anesthetized with sodium pentobarbital and radio transmitter (VM-FH, MiniMitter) was implanted into the peritoneal cavity. General activity was monitored using the Data Quest system (Data Science Intl.). The light conditions were identical to those used in the tissue culture experiments. After 2 weeks of entrainment, light:dark cycles were either advanced or delayed.

Figure 5:
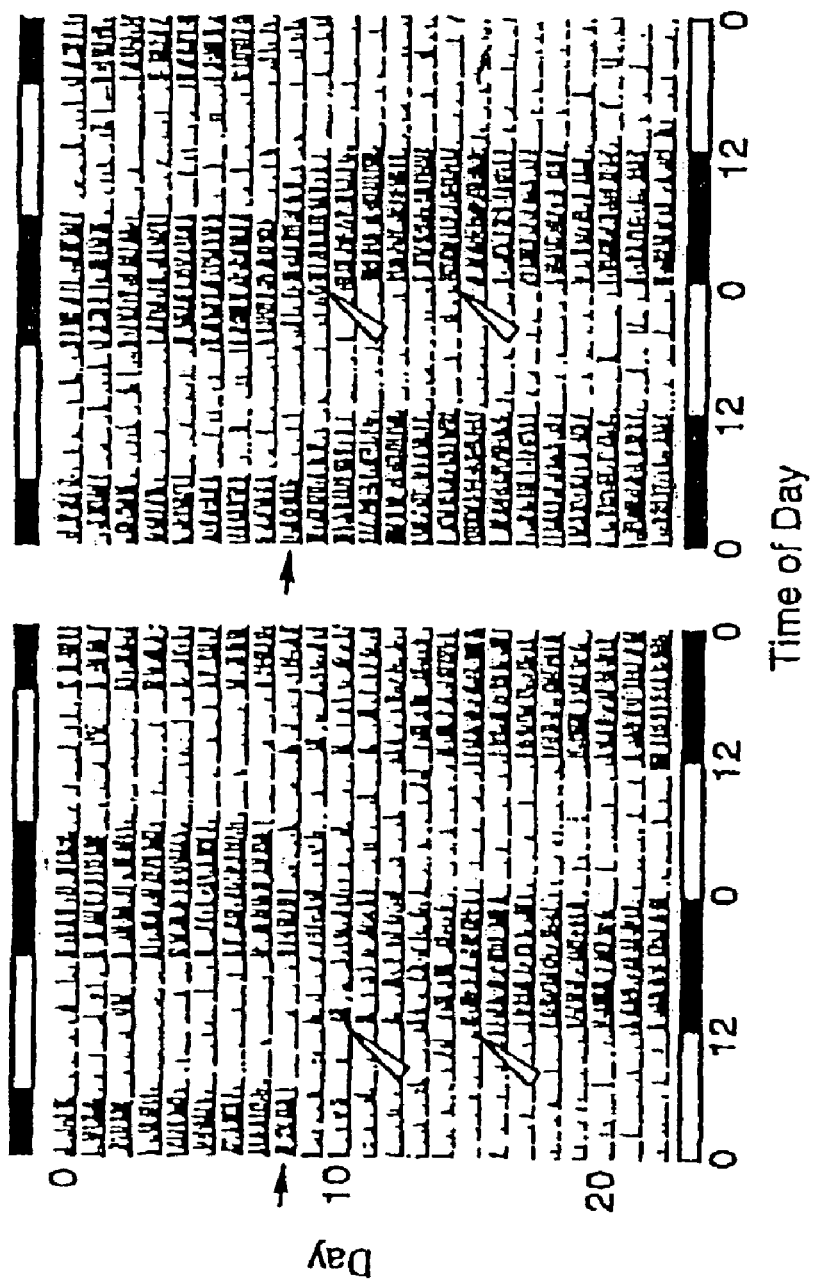
FIG. 5 shows representative locomotor activity records from Per1-luc transgenic rats in phase-advanced and phase-delayed light cycles. General activity was monitored with an implanted transmitter and has been double plotted. The original light:dark cycle (black and white bars at the top of figure) was shifted either 6 hours earlier (left panel) or 6 hours later (right panel) on the day indicated by the arrow (new light cycle indicated by black and white bars at bottom of figure). Note masking (the burst of activity) at light-off on first 5 cycles following the advance of the light cycle. This direct effect of the light to dark transition on locomotion is commonly observed in nocturnal rodents and does not indicate the phase of clock-controlled behavior. Complete re-entrainment as measured by visual inspection took about 6.2±0.5 cycles (SEM, n=10) following the phase advance or 1.8±0.3 cycles (SEM, n=10) following the phase delay. Shaded triangles indicate the time of sacrifice (on 1st and 6th cycles following the phase shift) of the mammals for which the time of SCN peak is plotted in FIG. 4. Similar phase shifting trajectories of locomotor rhythmicity have been previously observed in the same strain of Wistar rats "K. Honma, S. Honma, T. Hiroshige, *Biological Rhythms,* (Hokkaido University Press, Sapporo, 1989), in Japanese".

As with most behavioral or physiological circadian rhythms, the response of the rats' activity rhythms to these light cycled shifts was not immediate and was asymmetrical. Entrainment to the new phase occurred more rapidly following delays of the light cycle than following advances. This can be seen in the records of general activity of the transgenic rats shown in FIG. 5. Clearly behavioral rhythmicity shifted quite differently from the rhythmicity that measured from cultured SCN excised from identically treated mammals.

EXAMPLE 8

Detection of Rhythms of SCN from Transgenic Mice

Figure 6:
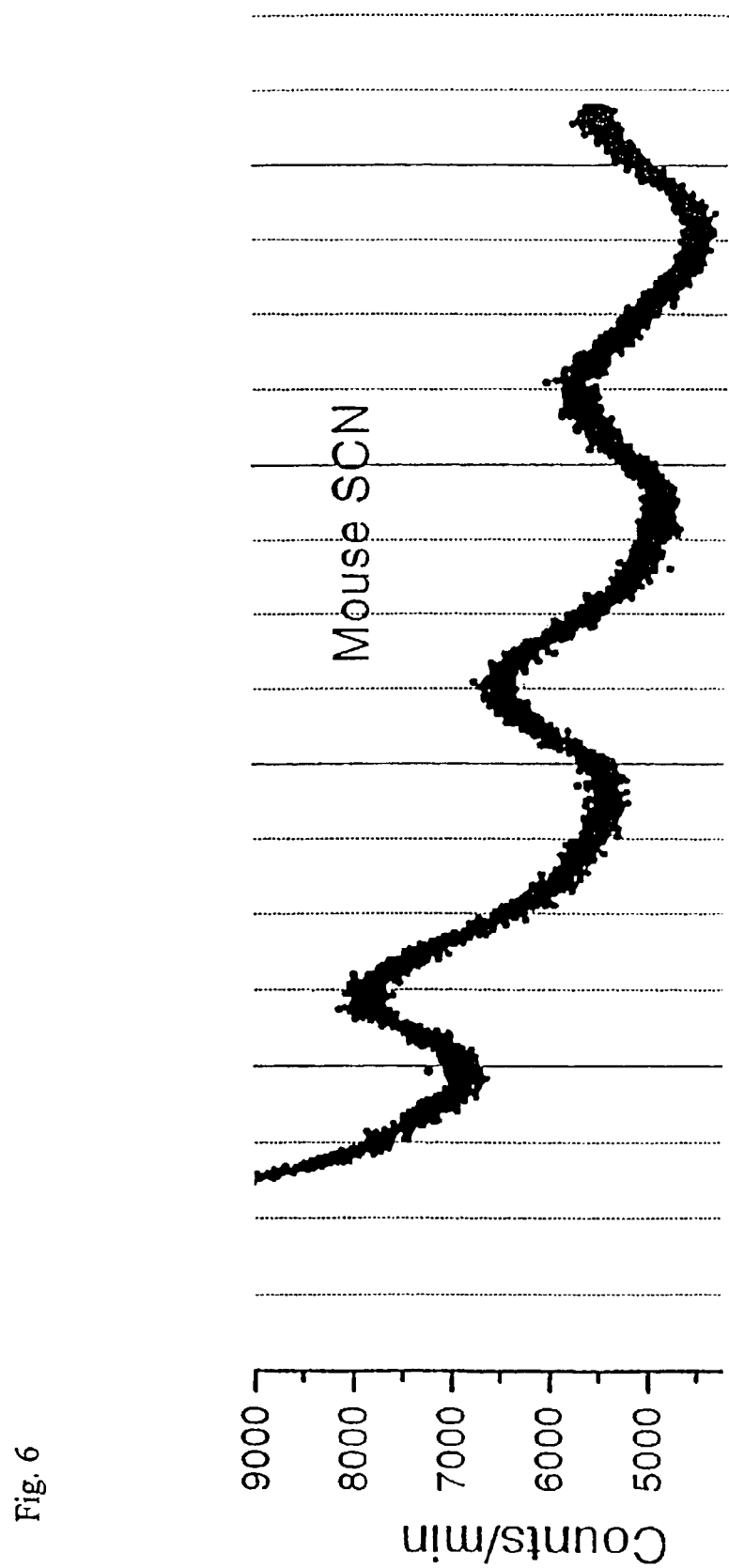
FIG. 6 shows a representative circadian rhythm of bioluminescence from a cultured SCN explanted from a Per1-luc transgenic mouse. Black and white bars show the animal's previous light:dark conditions. The explant was made just before light-off (arrow) and luminescence was monitored immediately. The near 24-h rhythm peaked in the middle of the subjective day and persisted for 4 days in vitro at which time the culture was removed from the assay.

Light emission from the SCN was invariably and robustly rhythmic, indicating that the engineered mPer1-luc transgene was being rhythmically transcribed under the control of normal circadian mechanisms (FIG. 6).

INDUSTRIAL APPLICABILITY

The present invention provides a DNA that rhythmically expresses a desired gene in compliance with the circadian rhythm. This invention also provides transgenic mammals that rhythmically express a desired gene in compliance with the circadian rhythm. The transgenic mammals of the invention can be used to monitor circadian oscillations in the central nervous system and peripheral tissues.

Rapid travel across several time zones and abrupt changes in work schedules both produce sudden large changes in input signals to the circadian system of humans by exposing the SCN to shifted light (and other environmental) cycles. The phase-shifting paradigm that is employed in the above Examples is closely analogous to trans-Atlantic flight from west to east (advance) and from east to west (delay).

In multi-cellular organisms, circadian oscillators are considered to be organized into multi-tissue systems which function as biological clocks that regulate the activities of the organism in relation to environmental cycles and provide an internal temporal framework. Mammals are relatively large in size, and several organs work in harmony within these. In the present invention, a lag was observed in the oscillation phase of these peripheral tissues compared with that of the SCN. If the phase relationships among the many rhythms that characterize circadian organization are adaptive, then disruption of those phase relationships will have deleterious consequences. That is likely to be the general explanation of the malaise that results from rapid trans-meridian travel, and more importantly from the shift work schedules to which more than 20% of the U.S. work force is exposed (U.S. Congress, Office of Technology Assessment, *Biological Rhythms: Implications for the Worker*, OTA-BA-463 (U.S. Government Printing Office, Washington, D.C., 1991).

The present invention enables one to analyze the relationship between the oscillations in intracerebral regions and peripheral nervous system, and also in peripheral organs and tissues, in addition to the central pacemaker, SCN. DNAs or transgenic mammals of the present invention are useful to screen a compound for treating disorders related to circadian rhythms, such as jet lag symptoms, shift-work sleep disorder, delayed sleep phase syndrome, and irregular sleep-wake disorder.

The invention claimed is:

1. An isolated Period 1 promoter DNA that induces rhythmical expression of a gene operably linked thereto in a mammal, wherein said Period 1 promoter DNA is selected from the group consisting of:
   (a) a nucleic acid comprising the nucleotide sequence from positions 23 to 6787 of SEQ ID NO: 1; and
   (b) a nucleic acid comprising the nucleotide sequence of SEQ ID NO: 2.

2. The isolated Period 1 promoter DNA of claim 1, wherein said Period 1 promoter DNA is a nucleic acid comprising the nucleotide sequence of SEQ ID NO: 2.

3. A recombinant DNA comprising the Period 1 promoter DNA according to claim 2 and a gene operably linked to said promoter, wherein said gene is rhythmically expressed under the control of said promoter in a mammal.

4. The recombinant DNA according to claim 3, wherein said gene is a luciferase gene, a green fluorescent protein (GFP) gene or a chloramphenicol acetyltransferase (CAT) gene.

5. The recombinant DNA according to claim 3, wherein said gene is a reporter gene.

6. An isolated cell comprising the recombinant DNA according to claim 3.

7. An isolated cell comprising the recombinant DNA according to claim 5.

8. A transgenic mouse or whose genome comprises a recombinant DNA comprising a Period 1 promoter DNA operably linked to a reporter gene, wherein said promoter induces rhythmical expression of a reporter gene operably linked thereto and wherein said Period 1 promoter DNA is a nucleic acid comprising the nucleotide sequence of SEQ ID NO: 2.

9. The transgenic mouse or rat according to claim 8, wherein said reporter gene is a luciferase gene, a green fluorescent protein (GFP) gene or a chloramphenicol acetyltransferase (CAT) gene.

10. A progeny of the transgenic mouse or rat according to claim 8, wherein the genome of said progeny comprises the recombinant DNA.

11. An isolated cell isolated from the transgenic mouse or rat according to claim 8, wherein said cell comprises the recombinant DNA.

12. An isolated tissue isolated from the transgenic mouse or rat of claim 8, wherein said tissue comprises the recombinant DNA.

13. A method of testing or screening a compound that has an activity to modify the expression of the transgene in the cell according to claim 6, comprising:
    (a) treating said cell with said compound;
    (b) measuring the expression of said transgene in the treated cell;
    (c) comparing the transgene expression after administration of the compound with that prior to the administration; and
    (d) selecting a compound that modifies the transgene expression.

14. A method of testing or screening for a pharmaceutical drug useful for treating a circadian rhythm sleep disorder, comprising:
    (a) treating the cell according to claim 7 with the pharmaceutical drug;
    (b) measuring the expression of the reporter gene in the cell;
    (c) comparing the reporter gene expression rhythm after administration of the compound with that prior to the administration; and
    (d) selecting a compound that modifies the phase, period or amplitude of the reporter gene expression rhythm following the treatment in (a), whereupon said compound is useful for treating a circadian rhythm sleep disorder.

15. A method of testing or screening a compound that has an activity to modify the expression of the transgene in the mouse or rat according to claim 8, comprising:
    (a) treating said mouse or rat with said compound;
    (b) measuring the expression of said transgene in the treated mouse or rat;
    (c) comparing the transgene expression rhythm after administration of the compound with that prior to the administration; and
    (d) selecting a compound that modifies the transgene expression.

16. A method of testing or screening for a pharmaceutical drug useful for treating a circadian rhythm sleep disorder, comprising:
    (a) treating the transgenic mouse or rat according to claim 8 with the pharmaceutical drug;
    (b) measuring the expression of the reporter gene in the treated transgenic mouse or rat;
    (c) comparing the reporter gene expression rhythm after administration of the compound with that prior to the administration; and
    (d) selecting a compound that modifies the phase, period or amplitude of the reporter gene expression rhythm following the treatment in (a), whereupon said compound is useful for treating a circadian rhythm sleep disorder.

17. A method of screening for a putative factor that regulates Period 1 expression, comprising the steps of:
    (a) administering a compound to a transgenic mouse or rat according to claim 8, whose circadian rhythm has already been determined;
    (b) periodically detecting expression level of the reporter gene in the transgenic mouse or rat and verifying the expression rhythm;
    (c) comparing the reporter gene expression rhythm after administration of the compound with that prior to the administration; and,
    (d) selecting a compound that modifies the phase, period or amplitude of the reporter gene expression rhythm, whereupon said factor regulates Period 1 expression.

18. A method of screening for a pharmaceutical drug useful for treating a circadian rhythm sleep disorder, comprising:
    (a) culturing the cell according to claim 11 or 12;
    (b) treating the cell with a compound for an appropriate period of time, and then continuing culturing;
    (c) periodically detecting reporter gene expression level; and
    (d) selecting a compound that modifies the phase, period or amplitude of the reporter gene expression rhythm following the treatment in (b), whereupon said compound is useful for treating a circadian rhythm sleep disorder.

19. A method of screening for a pharmaceutical drug useful for treating a circadian rhythm sleep disorder, comprising:
    (a) culturing the tissue according to claim 12;
    (b) treating the tissues with a compound for an appropriate period of time, and then continuing culturing;
    (c) periodically detecting reporter gene expression level; and
    (d) selecting a compound that modifies the phase, period or amplitude of the reporter gene expression rhythm following the treatment in (b), whereupon said compound is useful for treating a circadian rhythm sleep disorder.

* * * * *

UNITED STATES PATENT AND TRADEMARK OFFICE
CERTIFICATE OF CORRECTION

PATENT NO. : 7,659,387 B1  Page 1 of 1
APPLICATION NO. : 10/130659
DATED : February 9, 2010
INVENTOR(S) : Hajime Tei et al.

It is certified that error appears in the above-identified patent and that said Letters Patent is hereby corrected as shown below:

On the Title Page 1, Item (75) Inventors should read:
Michael Meneker, Charlottesville (VA).

On the Title Page 1, Item (73) Assignees should read:
University of Virginia, Madison Hall, Charlottesville, (VA); University of Virginia Patent Foundation, Charlottesville, (VA); Mitsubishi Pharma Corporation, Osaka (JP); Mitsubishi Tanabe Pharma Corporation, Osaka (JP).

On the Title Page:

The first or sole Notice should read --

Subject to any disclaimer, the term of this patent is extended or adjusted under 35 U.S.C. 154(b) by 54 days.

On the Title Page 1, Item (86) Priority Data should read:
PCT/JP00/08127, filed November 11, 2000, claiming the benefit of U.S.S.N. 60/166,383, Filed November 18, 1999.

Column 33, line 61, claim 8 should read:
A transgenic mouse or rat..........

Column 36, line 29, claim 18 should read:
(a) culturing the cell according to claims 11 or 7.

Signed and Sealed this

Fourteenth Day of December, 2010

David J. Kappos
*Director of the United States Patent and Trademark Office*

UNITED STATES PATENT AND TRADEMARK OFFICE
CERTIFICATE OF CORRECTION

PATENT NO. : 7,659,387 B1
APPLICATION NO. : 10/130659
DATED : February 9, 2010
INVENTOR(S) : Hajime Tei et al.

Page 1 of 1

It is certified that error appears in the above-identified patent and that said Letters Patent is hereby corrected as shown below:

On the Title Page 1, Item (75) Inventors should read:
Hajime Tei, Tokyo (JP); Yoshiyuki Sakaki, Yokohama (JP); Shin Yamazaki, Nashville, TN (US); Michikazu Abe, Tokyo (JP); Ri-ichi Takahashi, Tochigi (JP); Michael Meneker, Charlottesville, VA (US)

On the Title Page 1, Item (73) Assignees should read:
University of Virginia Patent Foundation, Charlottesville, VA (US);
Mitsubishi Tanabe Pharma Corporation, Osaka (JP)

On the Title Page:

The first or sole Notice should read --

Subject to any disclaimer, the term of this patent is extended or adjusted under 35 U.S.C. 154(b) by 54 days.

On the Title Page 1, Item (86) Priority Data should read:
PCT/JP00/08127, filed November 17, 2000, claiming the benefit of U.S.S.N. 60/166,383, Filed November 18, 1999.

Column 33, line 61, claim 8 should read:
A transgenic mouse or rat..........

Column 36, line 29, claim 18 should read:
(a) culturing the cell according to claims 11 or 7.

This certificate supersedes the Certificate of Correction issued December 14, 2010.

Signed and Sealed this
Fifteenth Day of March, 2011

David J. Kappos
*Director of the United States Patent and Trademark Office*